United States Patent
Hashida et al.

(10) Patent No.: US 9,891,188 B2
(45) Date of Patent: Feb. 13, 2018

(54) GAS CONCENTRATION DETECTING DEVICE

(71) Applicant: TOYOTA JIDOSHA KABUSHIKI KAISHA, Toyota-shi, Aichi-ken (JP)

(72) Inventors: Tatsuhiro Hashida, Shizuoka-ken (JP); Kazuhiro Wakao, Susono (JP); Keiichiro Aoki, Shizuoka-ken (JP)

(73) Assignee: TOYOTA JIDOSHA KABUSHIKI KAISHA, Toyota-shi (JP)

(*) Notice: Subject to any disclaimer, the term of this patent is extended or adjusted under 35 U.S.C. 154(b) by 188 days.

(21) Appl. No.: 14/840,482

(22) Filed: Aug. 31, 2015

(65) Prior Publication Data

US 2016/0061769 A1   Mar. 3, 2016

(30) Foreign Application Priority Data

Sep. 1, 2014   (JP) ................. 2014-177089

(51) Int. Cl.
*G01N 27/26* (2006.01)
*G01N 27/407* (2006.01)
*G01N 27/419* (2006.01)

(52) U.S. Cl.
CPC ....... *G01N 27/4074* (2013.01); *G01N 27/419* (2013.01)

(58) Field of Classification Search
None
See application file for complete search history.

(56) References Cited

U.S. PATENT DOCUMENTS

| 6,083,370 A * | 7/2000 | Kato ................. G01N 27/4065 204/425 |
| 6,319,377 B1 * | 11/2001 | Hasei .................. G01N 27/417 204/293 |
| 2008/0105545 A1 | 5/2008 | Nakagaki et al. |
| 2010/0243446 A1 | 9/2010 | Mizutani et al. |
| 2012/0285838 A1 * | 11/2012 | Liemersdorf ........ G01N 27/419 205/784 |
| 2016/0061771 A1 | 3/2016 | Mizutani et al. |

FOREIGN PATENT DOCUMENTS

| CN | 102639995 A | 8/2012 |
| EP | 0361692 A2 | 4/1990 |
| JP | H02-122255 A | 5/1990 |

(Continued)

OTHER PUBLICATIONS

US Patent and Trademark Office, Office Action issued to U.S. Appl. No. 14/840,382 dated Nov. 16, 2017, 13 pages.

*Primary Examiner* — Eli Mekhlin
(74) *Attorney, Agent, or Firm* — Andrews Kurth Kenyon LLP

(57) ABSTRACT

A gas concentration detecting device includes a gas concentration detecting element and an electronic control unit. The gas concentration detecting element includes a first electrochemical cell and a second electrochemical cell. The electronic control unit is configured to detect the concentration of the sulfur oxide contained in the test gas based on a first detected value correlated with a current flowing through the first electrochemical cell acquired when a first removing voltage is applied to the second electrochemical cell and a measuring voltage is applied to the first electrochemical cell.

14 Claims, 6 Drawing Sheets

(56) References Cited

FOREIGN PATENT DOCUMENTS

| | | |
|---|---|---|
| JP | H11-190721 A | 7/1999 |
| JP | 2001-116720 A | 4/2001 |
| JP | 2002-122255 A | 4/2002 |
| JP | 2011-190721 A | 9/2011 |
| JP | 2014-142199 A | 8/2014 |

* cited by examiner

GAS CONCENTRATION DETECTING DEVICE

INCORPORATION BY REFERENCE

The disclosure of Japanese Patent Application No. 2014-170547 filed on Sep. 1, 2014 including the specification, drawings and abstract is incorporated herein by reference in its entirety.

BACKGROUND OF THE INVENTION

1. Field of the Invention

The invention relates to a gas concentration detecting device that is capable of acquiring the accurate concentration of the sulfur oxide (SOx) contained in exhaust gas from an internal combustion engine.

2. Description of Related Art

An air-fuel ratio sensor (A/F sensor) that acquires the air-fuel ratio (A/F) of an air-fuel mixture in a combustion chamber based on the concentration of the oxygen ($O_2$) contained in exhaust gas so as to control an internal combustion engine is in wide use. A limiting current-type gas sensor is an example of this type of air-fuel ratio sensor.

The limiting current-type gas sensor used as the air-fuel ratio sensor described above is provided with a pumping cell that is an electrochemical cell which includes a solid electrolyte body having oxide ion conductivity and a pair of electrodes fixed to surfaces of the solid electrolyte body. One of the pair of electrodes is exposed to the exhaust gas from the internal combustion engine as test gas that is introduced via a diffusion resistance unit and the other one of the pair of electrodes is exposed to the atmosphere. When a voltage equal to or higher than a voltage at which the decomposition of oxygen is initiated (decomposition initiation voltage) is applied between the pair of electrodes with one of the pair of electrodes being a cathode and the other one of the pair of electrodes being an anode, the oxygen contained in the test gas becomes an oxide ion ($O^{2-}$) through reductive decomposition. This oxide ion is conducted to the anode via the solid electrolyte body, becomes oxygen, and is discharged into the atmosphere. This oxygen movement based on the conduction of the oxide ion via the solid electrolyte body from the cathode side to the anode side is referred to as an "oxygen pumping action".

The conduction of the oxide ion resulting from the oxygen pumping action causes a current flow between the pair of electrodes. This current that flows between the pair of electrodes is referred to as an "electrode current". This electrode current tends to become stronger as the voltage applied between the pair of electrodes (hereinafter, simply referred to as an "applied voltage" in some cases) increases. However, the flow rate of the test gas reaching the electrode (cathode) is limited by the diffusion resistance unit, and thus the rate of consumption of the oxygen resulting from the oxygen pumping action exceeds the rate of supply of the oxygen to the cathode soon. In other words, the reductive decomposition reaction of the oxygen in the cathode reaches a diffusion rate-controlled state.

In the diffusion rate-controlled state, the electrode current does not increase but remains substantially constant despite a rise in the applied voltage. The characteristics are referred to as "limiting current characteristics" and the range of the applied voltage in which the limiting current characteristics are expressed (observed) is referred to as a "limiting current region". The electrode current in the limiting current region is referred to as a "limiting current" and the magnitude of the limiting current (limiting current value) is correlated with the rate of the supply of the oxygen to the cathode. Since the flow rate of the test gas reaching the cathode is maintained to be constant by the diffusion resistance unit as described above, the rate of the supply of the oxygen to the cathode is correlated with the concentration of the oxygen contained in the test gas.

Accordingly, in the limiting current-type gas sensor used as the air-fuel ratio sensor, the electrode current (limiting current) pertaining to a case where the applied voltage is set to the "predetermined voltage in the limiting current region" is correlated with the concentration of the oxygen contained in the test gas. By using the limiting current characteristics of the oxygen described above, the air-fuel ratio sensor can detect the concentration of the oxygen contained in the test gas and acquire the air-fuel ratio of the air-fuel mixture in the combustion chamber based thereon.

The limiting current characteristics described above are not characteristics limited to oxygen gas. Specifically, the limiting current characteristics can be expressed based on an appropriate selection of the applied voltage and a cathode configuration in some of gases containing oxygen atoms in molecules (hereinafter, referred to as "oxygen-containing gases" in some cases). Examples of the oxygen-containing gases include sulfur oxide (SOx), water ($H_2O$), and carbon dioxide ($CO_2$).

A fuel for the internal combustion engine (such as light oil and gasoline) contains a small amount of a sulfur (S) component. Especially, a fuel that is also referred to as a poor fuel may have a relatively high sulfur component content. When the sulfur component content (hereinafter, simply referred to as a "sulfur content" in some cases) of a fuel is high, the likelihood of problems increases such as the degradation and/or malfunctioning of members constituting the internal combustion engine, poisoning of an exhaust gas purification catalyst, and generation of white smoke in the exhaust gas. Accordingly, it is desirable that the sulfur component content of the fuel is acquired so that the acquired sulfur content is, for example, reflected in controlling the internal combustion engine, used in issuing a warning relating to the malfunctioning of the internal combustion engine, or utilized in improving the on-board diagnosis (OBD) of the exhaust gas purification catalyst.

When the fuel for the internal combustion engine contains the sulfur component, sulfur oxide is contained in the exhaust gas that is discharged from the combustion chamber. In addition, the concentration of the sulfur oxide contained in the exhaust gas (hereinafter, simply referred to as a "SOx concentration" in some cases) increases as the content of the sulfur component in the fuel (sulfur content) increases. Accordingly, it is considered that an accurate sulfur content can be acquired based on the acquired SOx concentration when an accurate SOx concentration in the exhaust gas can be acquired.

In this technical field, attempts have been made to acquire the concentration of sulfur oxide contained in exhaust gas from an internal combustion engine by using the limiting current-type gas sensor that uses the oxygen pumping action described above. Specifically, a limiting current-type gas sensor (two cell- and limiting current-type gas sensor) is in use that is provided with two pumping cells which are arranged in series with cathodes facing each other in an internal space into which the exhaust gas from the internal combustion engine is introduced as test gas via the diffusion resistance unit.

In this sensor, the oxygen contained in the test gas is removed by the oxygen pumping action of the upstream-side pumping cell when a relatively low voltage is applied between the electrodes of the upstream-side pumping cells. In addition, the sulfur oxide contained in the test gas is subjected to reductive decomposition in the cathode by the downstream-side pumping cell when a relatively high voltage is applied between the electrodes of the downstream-side pumping cells, and the oxide ion that is generated as a result is conducted to the anode. The concentration of the sulfur oxide contained in the test gas is acquired based on the change in the electrode current value attributable to the oxygen pumping action (for example, refer to Japanese Patent Application Publication No. 11-190721).

SUMMARY OF THE INVENTION

As described above, attempts have been made in this technical field to acquire the concentration of sulfur oxide contained in exhaust gas from an internal combustion engine by using the limiting current-type gas sensor that uses the oxygen pumping action. However, the sulfur oxide that is contained in the exhaust gas has an extremely low level of concentration and the current (decomposition current) attributable to the decomposition of the sulfur oxide is extremely weak. In addition, decomposition currents attributable to oxygen-containing gases other than the sulfur oxide (such as water and carbon dioxide) can also flow between the electrodes. Accordingly, it is difficult to accurately distinguish and detect only the decomposition current that is attributable to the sulfur oxide.

The invention provides a gas concentration detecting device that is capable of acquiring the concentration of sulfur oxide contained in exhaust gas as test gas with the highest level of accuracy possible by using a limiting current-type gas sensor.

The inventor has conducted an intensive study so as to achieve the goal described above. As a result, it has been found out that an electrode current pertaining to a case where water and sulfur oxide are decomposed at a predetermined applied voltage in an electrochemical cell (pumping cell) capable of an oxygen pumping action changes in accordance with the concentration of the sulfur oxide in exhaust gas from an internal combustion engine as test gas.

More specifically, in the two cell-type limiting current-type gas sensor, the oxygen contained in the test gas is removed by the oxygen pumping action of the upstream-side pumping cell when a relatively low voltage is applied between the electrodes of the upstream-side pumping cell. In addition, the water and the sulfur oxide contained in the test gas are decomposed by the downstream-side pumping cell when a relatively high voltage is applied between the electrodes of the downstream-side pumping cell. In this case, the electrode current of the downstream-side pumping cell includes the decomposition current attributable to the water and the decomposition current attributable to the sulfur oxide.

In general, water in exhaust gas from an internal combustion engine has a higher concentration than sulfur oxide in the exhaust gas from the internal combustion engine, and thus the electrode current is stronger than the decomposition current that is attributable only to the sulfur oxide contained in the test gas and can be easily and accurately detected. The inventor has found out that the magnitude of this electrode current changes in accordance with the concentration of the sulfur oxide contained in the test gas. In addition, the electrode current of the downstream-side pumping cell does not include the decomposition current attributable to the oxygen according to this configuration since the oxygen contained in the test gas is removed by the upstream-side pumping cell. Accordingly, the inventor has reached a conclusion that the concentration of the sulfur oxide contained in the test gas can be accurately acquired based on the acquisition of a detected value correlated with the electrode current.

In some cases, nitrogen oxide (NOx) is contained in exhaust gas from an internal combustion engine and the concentration of the nitrogen oxide (hereinafter, simply referred to as a "NOx concentration" in some cases) changes depending on the air-fuel ratio and combustion state of an air-fuel mixture combusted in a combustion chamber of the internal combustion engine. This nitrogen oxide is also decomposed by a downstream-side pumping cell and a decomposition current attributable to the nitrogen oxide is generated. Accordingly, it is desirable that the nitrogen oxide contained in the test gas is removed by an upstream-side pumping cell for an accurate concentration of sulfur oxide contained in the test gas to be acquired.

According to an aspect of the invention, there is provided a gas concentration detecting device including a gas concentration detecting element, a first current detector, a first electric power supply, a second electric power supply and an electronic control unit (ECU).

The gas concentration detecting element includes a first electrochemical cell, a second electrochemical cell, a dense body and a diffusion resistance unit. The first electrochemical cell includes a first solid electrolyte body, a first electrode and a second electrode. The first solid electrolyte body has oxide ion conductivity. The first electrode and the second electrode are arranged on respective surfaces of the first solid electrolyte body. The second electrochemical cell includes a second solid electrolyte body, a third electrode, and a fourth electrode. The second solid electrolyte body has oxide ion conductivity. The third electrode and the fourth electrode are arranged on respective surfaces of the second solid electrolyte body. The first solid electrolyte body and the second solid electrolyte body may be separate solid electrolyte bodies (such as sheet bodies). Alternatively, the first electrochemical cell and the second electrochemical cell may share a single solid electrolyte body (such as a sheet body).

The first solid electrolyte body, the second solid electrolyte body, the dense body and the diffusion resistance unit are configured to define an internal space. The diffusion resistance unit is configured to introduce exhaust gas from an internal combustion engine as test gas into the internal space via the diffusion resistance unit. The first electrode is exposed to the internal space. The second electrode is exposed to a first separate space as a space other than the internal space. The third electrode is arranged at a position in the internal space closer to the diffusion resistance unit than the first electrode is. The fourth electrode is exposed to a second separate space as a space other than the internal space. The first electrode is configured to decompose water and sulfur oxide contained in the test gas when a voltage equal to or higher than a first predetermined voltage is applied to a first electrode pair of the first electrode and the second electrode. The third electrode is configured to decompose oxygen and nitrogen oxide contained in the test gas when a voltage equal to or higher than a second predetermined voltage is applied to a second electrode pair of the third electrode and the fourth electrode.

The first current detector is configured to output a first detected value correlated with a current flowing through the first electrode pair. The first electric power supply is configured to apply a voltage to the first electrode pair. The second electric power supply is configured to apply a voltage to the second electrode pair. The ECU is configured to control the second electric power supply such that a first removing voltage is applied to the second electrode pair. The first removing voltage is a voltage equal to or higher than the second predetermined voltage, a voltage equal to or higher than a lower limit of a voltage range in which a limiting current characteristics of nitrogen oxide are expressed in the third electrode, and a voltage lower than a voltage at which a decomposition of sulfur oxide is initiated. The ECU is configured to control the first electric power supply such that a measuring voltage is applied to the first electrode pair. The measuring voltage is a voltage equal to or higher than the first predetermined voltage and a voltage equal to or higher than a voltage at which a decomposition of water is initiated in the first electrode. The ECU is configured to acquire the first detected value from the first current detector when the first removing voltage is applied to the second electrode pair and the measuring voltage is applied to the first electrode pair. The ECU is configured to detect the concentration of the sulfur oxide contained in the test gas based on the acquired first detected value.

According to the gas concentration detecting device of the aspect described above, the first electrode is configured to be capable of decomposing the water and the sulfur oxide contained in the test gas when a voltage equal to or higher than the first predetermined voltage is applied between the first electrode and the second electrode. The first electrode that is capable of decomposing the water and the sulfur oxide at a predetermined applied voltage as described above can be produced by appropriately selecting, for example, the type of a substance constituting an electrode material and a heat treatment condition pertaining to the production of the electrode.

The third electrode is configured to be capable of decomposing the oxygen and the nitrogen oxide contained in the test gas when a voltage equal to or higher than the second predetermined voltage is applied between the third electrode and the fourth electrode. The third electrode that is capable of decomposing the oxygen and the nitrogen oxide at a predetermined applied voltage as described above can be produced by appropriately selecting, for example, the type of a substance constituting an electrode material and a heat treatment condition pertaining to the production of the electrode.

The ECU controls the second electric power supply so that the predetermined first removing voltage, which is a voltage equal to or higher than the second predetermined voltage, a voltage equal to or higher than the lower limit of the voltage range in which the limiting current characteristics of the nitrogen oxide are expressed in the third electrode, and a voltage lower than the voltage at which the decomposition of the sulfur oxide is initiated, is applied to the second electrode pair. Accordingly, the limiting current characteristics of the oxygen and the nitrogen oxide contained in the test gas are expressed and the oxygen and the nitrogen oxide contained in the test gas are discharged from the internal space when the first removing voltage is applied to the second electrode pair. The water and the sulfur oxide contained in the test gas are not decomposed in the third electrode to which the first removing voltage is applied.

The ECU controls the first electric power supply so that the predetermined measuring voltage, which is a voltage equal to or higher than the first predetermined voltage and a voltage equal to or higher than the voltage at which the decomposition of the water is initiated in the first electrode, is applied to the first electrode pair. The "voltage at which the decomposition of the water is initiated" is higher than the "voltage at which the decomposition of the sulfur oxide is initiated". Accordingly, an electrode current that is attributable to the decomposition of the water and the sulfur oxide contained in the test gas flows between the electrodes when the measuring voltage is applied to the first electrode pair. The magnitude of this electrode current changes in accordance with the concentration of the sulfur oxide contained in the test gas as described above.

The ECU is configured to detect the concentration of the sulfur oxide contained in the test gas based on the first detected value that is acquired in a case where the first removing voltage is applied to the second electrode pair and the measuring voltage is applied to the first electrode pair. As described above, the first removing voltage is a predetermined voltage that is a voltage equal to or higher than the second predetermined voltage, a voltage equal to or higher than the lower limit of the voltage range in which the limiting current characteristics of the nitrogen oxide are expressed in the third electrode, and a voltage lower than the voltage at which the decomposition of the sulfur oxide is initiated. Accordingly, the limiting current characteristics of the oxygen and the nitrogen oxide are expressed and the oxygen and the nitrogen oxide contained in the test gas are removed by an oxygen pumping action of the second electrochemical cell in a case where the first removing voltage is applied to the second electrode pair.

The measuring voltage is a predetermined voltage that is a voltage equal to or higher than the first predetermined voltage and a voltage equal to or higher than the voltage at which the decomposition of the water is initiated in the first electrode. Accordingly, in a case where the measuring voltage is applied to the first electrode pair, the water and the sulfur oxide contained in the test gas are decomposed by the first electrochemical cell and a decomposition current attributable to these components flows as an electrode current. In addition, not only the oxygen contained in the test gas but also the nitrogen oxide contained in the test gas is removed from the test gas by the second electrochemical cell on the upstream side of the first electrochemical cell in the internal space. Accordingly, the magnitude of this electrode current changes in accordance with the concentration of the sulfur oxide contained in the test gas without being affected by the oxygen and the nitrogen oxide contained in the test gas during the introduction into the internal space.

In other words, the ECU can accurately acquire the concentration of the sulfur oxide contained in the test gas based on the first detected value. More specifically, the ECU can specify a SOx concentration correlated with the acquired first detected value based on, for example, a correspondence relationship between the concentration of the sulfur oxide contained in the test gas (SOx concentration) acquired in advance and the first detected value. In this manner, the concentration of the sulfur oxide contained in the test gas can be detected with a very high level of accuracy.

In this case, the correspondence relationship between the first detected value (such as the magnitude of the electrode current) that is acquired in a case where, for example, the first removing voltage is applied to the second electrode pair and the measuring voltage is applied to the first electrode pair and the concentration of the sulfur oxide contained in the test gas is obtained in advance by a prior experiment or the like. A data table (such as a data map) showing the correspondence relationship can be stored in, for example, a data storage device (such as a ROM) of the ECU so that a CPU can refer to the data table during the detection. In this manner, the concentration of the sulfur oxide contained in the test gas can be specified from the first detected value.

The concentration of the water contained in the exhaust gas discharged from the internal combustion engine changes in accordance with, for example, the air-fuel ratio of an air-fuel mixture combusted in a combustion chamber of the internal combustion engine. When the concentration of the water contained in the exhaust gas from the internal combustion engine as the test gas changes, the accuracy of the concentration of the sulfur oxide detected based on the first detected value may be reduced. Accordingly, it is desirable that the first detected value is detected when the air-fuel ratio of the air-fuel mixture combusted in the combustion chamber of the internal combustion engine is maintained at a predetermined value, examples of which include during a steady operation of the internal combustion engine, for the concentration of the sulfur oxide contained in the test gas to be accurately detected based on the first detected value.

Details of a mechanism in which the first detected value acquired in a case where the measuring voltage is applied between the first electrode and the second electrode as described above changes in accordance with the concentration of the sulfur oxide in the test gas are unknown. However, not only the water contained in the test gas but also the sulfur oxide contained in the test gas is decomposed when the measuring voltage is applied to the first electrode pair as described above. As a result, it is considered that the decomposition product of the sulfur oxide (examples including sulfur (S) and a sulfur compound) adsorbs to the first electrode, which is a cathode, and decreases the area of the first electrode capable of contributing to the decomposition of water. Accordingly, it is considered that the first detected value, which is correlated with the electrode current pertaining to the application of the first predetermined voltage to the first electrode pair, changes in accordance with the concentration of the sulfur oxide contained in the test gas.

According to the mechanism described above, a larger amount of the decomposition product of the sulfur oxide adsorbs to the first electrode and the rate of reduction in the electrode current correlated with the first detected value increases as the period in which the measuring voltage is applied to the first electrode pair extends. In other words, the rate of reduction in the electrode current correlated with the first detected value changes in accordance with the length of the period in which the measuring voltage is applied to the first electrode pair. Accordingly, it is desirable that the first detected value is detected at a point in time when the measuring voltage is applied to the first electrode pair over a predetermined period determined in advance for the concentration of the sulfur oxide contained in the test gas to be accurately detected based on the first detected value. In addition, it is desirable that the correspondence relationship between the SOx concentration and the first detected value described above is acquired by using the first detected value at a point in time when the measuring voltage is applied to the first electrode pair over a predetermined period determined in advance.

In addition, the decomposition product adsorbing to the first electrode needs to be removed in a case where the concentration of the sulfur oxide contained in the test gas is to be detected again after the use in detecting the concentration of the sulfur oxide contained in the test gas. A method for removing the decomposition product adsorbing to the first electrode is not particularly limited, and examples thereof can include reoxidizing the decomposition product so that the decomposition product turns back into sulfur oxide. This reoxidation can be performed by, for example, applying a predetermined voltage that allows the decomposition product to be reoxidized to the first electrode pair with the first electrode being an anode and the second electrode being a cathode (which is opposite to the case of the reductive decomposition of sulfur oxide).

The first detected value is not particularly limited insofar as the first detected value is the value of any signal correlated with the electrode current (examples including a voltage value, a current value, and a resistance value). Typically, the first detected value may be a magnitude of the current flowing through the first electrode pair. In other words, the ECU may be configured to acquire the magnitude of the current flowing through the first electrode pair as the first detected value.

As described above, the magnitude of the electrode current flowing between the first electrode and the second electrode in a case where the measuring voltage is applied between the first electrode and the second electrode changes in accordance with the concentration of the sulfur oxide contained in the test gas. Specifically, the electrode current weakens as the concentration of the sulfur oxide contained in the test gas increases as described later. Accordingly, the ECU may be configured to detect a higher value of the concentration of the sulfur oxide (SOx) contained in the test gas as the first detected value acquired in a case where the first removing voltage is applied to the second electrode pair and the measuring voltage is applied to the first electrode pair decreases in a case where the magnitude of the current flowing through the first electrode pair is the first detected value as described above.

As described above, the limiting current characteristics of the oxygen are expressed in a case where the first removing voltage is applied to the second electrode pair of the second electrochemical cell. As described in the beginning of this specification, the magnitude of the limiting current changes in accordance with the concentration of the oxygen contained in the test gas, and thus the concentration of the oxygen contained in the test gas can be detected with the limiting current characteristics of the oxygen.

The ECU may be configured to acquire a second detected value correlated with a current flowing through the second electrode pair. In this case, the ECU may be configured to detect the concentration of the oxygen contained in the test gas based on the second detected value acquired in a case where the first removing voltage is applied to the second electrode pair.

According to the aspect described above, both the concentration of the sulfur oxide contained in the test gas and the concentration of the oxygen contained in the test gas can be detected. In addition, the air-fuel ratio of the air-fuel mixture combusted in the combustion chamber of the internal combustion engine may be acquired based on the oxygen concentration acquired in this manner. Accordingly, this allows, for example, a control system for the internal combustion engine to be reduced in cost and/or size.

The concentration of the oxygen contained in the test gas is detected based on the second detected value correlated with the current flowing through the second electrode pair when the first removing voltage is applied to the second electrode pair. The first removing voltage is a predetermined voltage that is a voltage equal to or higher than the second predetermined voltage, a voltage equal to or higher than the lower limit of the voltage range in which the limiting current characteristics of the nitrogen oxide are expressed in the third electrode, and a voltage lower than the voltage at which the decomposition of the sulfur oxide is initiated. The third electrode is configured to be capable of decomposing the oxygen and the nitrogen oxide contained in the test gas when the first removing voltage is applied to the second electrode pair. Accordingly, not only the limiting current of the oxygen but also the limiting current of the nitrogen oxide is included in the electrode current correlated with the second detected value.

In other words, strictly speaking, not only the concentration of the oxygen but also the concentration of the nitrogen oxide is included in the concentration of the oxygen detected as described above. However, the concentration of the nitrogen oxide contained in the test gas is sufficiently lower than the concentration of the oxygen. Accordingly, no significant problem arises regarding general applications (such as the calculation of the air-fuel ratio of the air-fuel mixture) even when the concentration of the oxygen detected as described above is regarded as the concentration of the oxygen alone.

The second detected value described above is not particularly limited insofar as the second detected value is the value of any signal correlated with the electrode current (examples including a voltage value, a current value, and a resistance value). Typically, the second detected value may be the magnitude of the current flowing through the second electrode pair. In other words, the ECU may be configured to acquire the magnitude of the current flowing through the second electrode pair as the second detected value.

The electrode current that flows between these electrodes in a case where the first removing voltage is applied to the second electrode pair is the limiting current of the oxygen (and the nitrogen oxide) contained in the test gas, and the magnitude of the limiting current changes in accordance with the concentration of the oxygen contained in the test gas as described in the beginning of this specification. Specifically, the limiting current becomes stronger as the concentration of the oxygen contained in the test gas increases. Accordingly, the ECU may be configured to detect a higher value of the concentration of the oxygen contained in the test gas as the second detected value acquired in a case where the first removing voltage is applied to the second electrode pair increases in a case where the magnitude of the current flowing through the second electrode pair is the second detected value as described above.

In the aspect described above, both the oxygen and the nitrogen oxide contained in the test gas are removed by the pumping cell (second electrochemical cell) on the upstream side. The device according to the invention, however, can also be configured to remove the oxygen and the nitrogen oxide contained in the test gas with separate pumping cells.

In this case, the gas concentration detecting element may be further provided with a third electrochemical cell that includes a third solid electrolyte body that has oxide ion conductivity, and a fifth electrode and a sixth electrode which are formed on respective surfaces of the third solid electrolyte body. The third solid electrolyte body may be a solid electrolyte body (such as a sheet body) separate from the first solid electrolyte body and the second solid electrolyte body. Alternatively, the third electrochemical cell may share a solid electrolyte body (such as a sheet body) with any one or both of the first electrochemical cell and the second electrochemical cell.

The gas concentration detecting element may be configured for the fifth electrode to be exposed to the internal space being arranged at a position closer to the diffusion resistance unit than the third electrode and for the sixth electrode to be exposed to a third separate space as a space other than the internal space. In other words, the fifth electrode may be formed at a position in the internal space that is on the further upstream side than the third electrode (side close to the diffusion resistance unit). In other words, the third electrochemical cell may be formed on the further upstream side than the second electrochemical cell.

In the aspect described above, the ECU may control a third electric power supply so that a voltage is applied to a third electrode pair of the fifth electrode and the sixth electrode. The ECU may be an ECU for an internal combustion engine that applies a predetermined voltage to each electrode of the third electrode pair by controlling the electric power supplied from a battery or the like.

The fifth electrode may be configured to be capable of decomposing oxygen without decomposing the nitrogen oxide contained in the test gas when a voltage equal to or higher than a third predetermined voltage is applied to the third electrode pair. The fifth electrode that is capable of decomposing the oxygen without decomposing the nitrogen oxide at a predetermined applied voltage as described above can be produced by appropriately selecting, for example, the type of a substance constituting an electrode material and a heat treatment condition pertaining to the production of the electrode.

The ECU may control the third electric power supply so that a predetermined second removing voltage is applied to the third electrode pair, the second removing voltage being a voltage equal to or higher than the third predetermined voltage, a voltage equal to or higher than the lower limit of the voltage range in which the limiting current characteristics of the oxygen are expressed in the fifth electrode, and a voltage lower than the voltage at which the decomposition of the sulfur oxide is initiated.

The ECU may be configured to detect the concentration of the sulfur oxide contained in the test gas based on the first detected value acquired in a case where the second removing voltage is applied to the third electrode pair, the first removing voltage is applied to the second electrode pair, and the measuring voltage is applied to the first electrode pair.

The limiting current characteristics of the oxygen contained in the test gas are expressed and the oxygen contained in the test gas is discharged from the internal space by an oxygen pumping action of the third electrochemical cell when the second removing voltage is applied to the third electrode pair. The limiting current characteristics of the nitrogen oxide contained in the test gas are expressed and the nitrogen oxide contained in the test gas is discharged from the internal space by the oxygen pumping action of the second electrochemical cell when the first removing voltage is applied to the second electrode pair. As a result, substantially no oxygen or nitrogen oxide is contained in the test gas reaching the first electrode of the first electrochemical cell arranged on the most downstream side. Accordingly, the first detected value acquired by the ECU changes in accordance with the concentration of the sulfur oxide contained in the test gas without being affected by the oxygen and the nitrogen oxide contained in the test gas during the introduction into the internal space.

In other words, the ECU can accurately acquire the concentration of the sulfur oxide contained in the test gas based on the first detected value. More specifically, the ECU can specify a SOx concentration correlated with the acquired first detected value based on, for example, a correspondence relationship between the concentration of the sulfur oxide contained in the test gas (SOx concentration) acquired in advance and the first detected value. In this manner, the concentration of the sulfur oxide contained in the test gas can be detected with a very high level of accuracy.

The oxygen contained in the test gas is discharged from the internal space by the oxygen pumping action of the third electrochemical cell and the nitrogen oxide contained in the test gas is discharged from the internal space by the oxygen pumping action of the second electrochemical cell. Accordingly, the concentration of the oxygen contained in the test gas can be detected based on the detected value correlated with the electrode current attributable to the decomposition of the oxygen in the third electrochemical cell. Likewise, the concentration of the nitrogen oxide contained in the test gas can be detected based on the detected value correlated with the electrode current attributable to the decomposition of the nitrogen oxide in the second electrochemical cell.

In this case, a second current detector that outputs the second detected value correlated with the current flowing through the second electrode pair and a third current detector that outputs a third detected value correlated with a current flowing through the third electrode pair may be provided.

The ECU may be configured to detect the concentration of the nitrogen oxide contained in the test gas based on the second detected value acquired when the second predetermined voltage is applied to the second electrode pair. More specifically, the ECU may specify a NOx concentration correlated with the acquired second detected value based on, for example, a correspondence relationship between the concentration of the nitrogen oxide contained in the test gas (NOx concentration) acquired in advance and the second detected value.

In addition, the ECU may be configured to detect the concentration of the oxygen contained in the test gas based on the third detected value acquired when the third predetermined voltage is applied to the third electrode pair. The air-fuel ratio of the air-fuel mixture combusted in the combustion chamber of the internal combustion engine may be acquired based on the oxygen concentration acquired in this manner.

The second current detector may be, for example, detecting means (such as a sensor) for outputting the second detected value correlated with the current flowing through the second electrode pair (examples including a current value, a voltage value, and a resistance value). The third current detector may be, for example, detecting means (such as a sensor) for outputting the third detected value correlated with the current flowing through the third electrode pair (examples including a current value, a voltage value, and a resistance value). The ECU may be configured to receive output signals of the second detected value and the third detected value from the second current detector and the third current detector.

In this manner, the concentration of the sulfur oxide contained in the test gas can be detected and the concentration of the oxygen contained in the test gas and the concentration of the nitrogen oxide contained in the test gas can be individually detected. Accordingly, this allows, for example, the control system for the internal combustion engine to be reduced in cost and/or size.

The third detected value described above is not particularly limited insofar as the third detected value is the value of any signal correlated with the current flowing through the third electrode pair (examples including a voltage value, a current value, and a resistance value). Typically, the third detected value may be the magnitude of the current flowing through the third electrode pair. In other words, the ECU may be configured to acquire the magnitude of the current flowing through the third electrode pair as the third detected value.

The electrode current that flows between these electrodes in a case where the second removing voltage is applied to the third electrode pair is the limiting current of the oxygen contained in the test gas, and the magnitude of the limiting current changes in accordance with the concentration of the oxygen contained in the test gas as described in the beginning of this specification. Specifically, the limiting current becomes stronger as the concentration of the oxygen contained in the test gas increases. Accordingly, the ECU may be configured to detect a higher value of the concentration of the oxygen contained in the test gas as the third detected value acquired when the second removing voltage is applied to the third electrode pair increases in a case where the magnitude of the current flowing through the third electrode pair is the third detected value as described above.

The second detected value described above is not particularly limited insofar as the second detected value is the value of any signal correlated with the current flowing through the second electrode pair (examples including a voltage value, a current value, and a resistance value). Typically, the second detected value may be the magnitude of the current flowing through the second electrode pair. In other words, the ECU may be configured to acquire the magnitude of the current flowing through the second electrode pair as the second detected value.

The electrode current that flows between these electrodes in a case where the first removing voltage is applied to the second electrode pair is the limiting current of the nitrogen oxide contained in the test gas, and the magnitude of the limiting current changes in accordance with the concentration of the nitrogen oxide contained in the test gas. Specifically, the limiting current becomes stronger as the concentration of the nitrogen oxide contained in the test gas increases. Accordingly, the ECU may be configured to detect a higher value of the concentration of the nitrogen oxide contained in the test gas as the second detected value acquired when the first removing voltage is applied to the second electrode pair increases in a case where the magnitude of the current flowing through the second electrode pair is the second detected value as described above.

In the aspect described above, the third electrochemical cell is arranged on the further upstream side of the second electrochemical cell. In other words, the second electrochemical cell and the third electrochemical cell are arranged in series. However, the second electrochemical cell and the third electrochemical cell may be arranged in parallel.

Herein, the "parallel" is not limited to a case where the second electrochemical cell and the third electrochemical cell are arranged in parallel in a geometric sense. Specifically, the "parallel" described above may be a broad concept including a case where the second electrochemical cell and the third electrochemical cell are arranged for the concentration of the oxygen contained in the test gas reaching the second electrochemical cell to be substantially equal to the concentration of the oxygen contained in the test gas reaching the third electrochemical cell.

In this case, the gas concentration detecting element may be further provided with a third electrochemical cell that includes a third solid electrolyte body that has oxide ion conductivity, and a fifth electrode and a sixth electrode which are formed on respective surfaces of the third solid electrolyte body. The third solid electrolyte body may be a solid electrolyte body (such as a sheet body) separate from the first solid electrolyte body and the second solid electrolyte body. Alternatively, the third electrochemical cell may share a solid electrolyte body (such as a sheet body) with any one or both of the first electrochemical cell and the second electrochemical cell.

The gas concentration detecting element may be configured for the fifth electrode to be exposed to the internal space being arranged in a region reached by test gas containing oxygen with the concentration equal to the concentration of the oxygen contained in the test gas reaching the third electrode and for the sixth electrode to be exposed to a third separate space as a space other than the internal space.

The voltage application to the third electrode pair by the third electric power supply, the configuration of the fifth electrode that allows the oxygen contained in the test gas to be decomposed without the decomposition of the nitrogen oxide contained in the test gas when the third predetermined voltage is applied to the third electrode pair, and the configuration of the ECU that allows the third electric power supply to be controlled for the application of the predetermined second removing voltage, which is a voltage equal to or higher than the third predetermined voltage, a voltage equal to or higher than the lower limit of the voltage range in which the limiting current characteristics of the oxygen are expressed in the fifth electrode, and a voltage lower than the voltage at which the decomposition of the sulfur oxide is initiated, to the third electrode pair are common to the above-described aspect in which the second electrochemical cell and the third electrochemical cell are arranged in series.

In addition, the configuration of the ECU that allows the concentration of the sulfur oxide contained in the test gas to be detected based on the first detected value acquired when the second removing voltage is applied to the third electrode pair, the first removing voltage is applied to the second electrode pair, and the measuring voltage is applied to the first electrode pair is common to the above-described aspect in which the second electrochemical cell and the third electrochemical cell are arranged in series.

In other words, even in this case, substantially no oxygen or nitrogen oxide is contained in the test gas reaching the first electrode of the first electrochemical cell arranged on the most downstream side. Accordingly, the first detected value acquired by the ECU changes in accordance with the concentration of the sulfur oxide contained in the test gas without being affected by the oxygen and the nitrogen oxide contained in the test gas during the introduction into the internal space. Accordingly, the ECU can accurately acquire the concentration of the sulfur oxide contained in the test gas based on the first detected value.

In the aspect described above, the oxygen contained in the test gas is discharged from the internal space by the oxygen pumping action of the third electrochemical cell and the oxygen and the nitrogen oxide contained in the test gas are discharged from the internal space by the oxygen pumping action of the second electrochemical cell. Accordingly, the electrode current in the third electrochemical cell is attributable to the decomposition current of the oxygen and the electrode current in the second electrochemical cell is attributable to the decomposition currents of the oxygen and the nitrogen oxide.

As described above, the concentration of the oxygen contained in the test gas reaching the second electrochemical cell and the concentration of the oxygen contained in the test gas reaching the third electrochemical cell are substantially equal to each other. Accordingly, the difference between the second detected value correlated with the electrode current in the second electrochemical cell and the third detected value correlated with the electrode current in the third electrochemical cell reflects the concentration of the nitrogen oxide contained in the test gas reaching the second electrochemical cell. In other words, the concentration of the oxygen contained in the test gas can be detected based on the third detected value and the concentration of the nitrogen oxide contained in the test gas can be detected based on the difference between the second detected value and the third detected value.

In this case, a second current detector that outputs the second detected value correlated with the current flowing through the second electrode pair and a third current detector that outputs a third detected value correlated with a current flowing through the third electrode pair may be further provided.

The ECU may be configured to detect the concentration of the oxygen contained in the test gas based on the third detected value acquired in a case where the second removing voltage is applied to the third electrode pair. The air-fuel ratio of the air-fuel mixture combusted in the combustion chamber of the internal combustion engine may be acquired based on the oxygen concentration acquired in this manner.

The ECU may be configured to detect the concentration of the nitrogen oxide contained in the gas based on the difference between the second detected value and the third detected value. The third detected value is the third detected value that is acquired when the second removing voltage is applied to the third electrode pair and the second detected value is the second detected value that is acquired in a case where the first removing voltage is applied to the second electrode pair. The ECU can specify a NOx concentration correlated with the acquired difference between the second detected value and the third detected value based on, for example, a correspondence relationship between the concentration of the nitrogen oxide contained in the test gas (NOx concentration) acquired in advance and the "difference between the second detected value and the third detected value".

As described above, the device according to the invention allows the concentration of the sulfur oxide contained in the test gas to be detected and allows the concentration of the oxygen contained in the test gas and the concentration of the nitrogen oxide contained in the test gas to be individually detected. Accordingly, this allows, for example, a control system for the internal combustion engine to be reduced in cost and/or size.

The third current detector described above may be configured to acquire the magnitude of the current flowing through the third electrode pair as the third detected value. The ECU can be configured to detect a higher value of the concentration of the oxygen contained in the test gas as the third detected value acquired in a case where the third predetermined voltage is applied to the third electrode pair increases in a case where the magnitude of the current flowing through the third electrode pair is the third detected value as described above.

The second current detector may be configured to acquire the magnitude of the current flowing through the second electrode pair as the second detected value. The ECU can be configured to detect a higher value of the concentration of the nitrogen oxide contained in the test gas as the second detected value acquired in a case where the first removing voltage is applied to the second electrode pair increases in a case where the magnitude of the current flowing through the second electrode pair is the second detected value as described above.

As described above, the fifth electrode may be configured to be capable of decomposing oxygen without decomposing the nitrogen oxide contained in the test gas when a voltage equal to or higher than the third predetermined voltage is applied to the third electrode pair. The fifth electrode that is capable of decomposing the oxygen without decomposing the nitrogen oxide at a predetermined applied voltage as described above can also be produced by appropriately selecting, for example, the type of a substance constituting an electrode material and a heat treatment condition pertaining to the production of the electrode. Typically, it is desirable that the fifth electrode contains at least one selected from the group consisting of platinum (Pt), gold (Au), lead (Pb), and silver (Ag).

As described above, the third electrode may be configured to be capable of decomposing the oxygen and the nitrogen oxide contained in the test gas when a voltage equal to or higher than the second predetermined voltage is applied to the second electrode pair. The third electrode that is capable of decomposing the oxygen and the nitrogen oxide at a predetermined applied voltage as described above can be produced by appropriately selecting, for example, the type of a substance constituting an electrode material and a heat treatment condition pertaining to the production of the electrode. Examples of the material constituting the third electrode include a substance (such as a precious metal) that has activity so that the oxygen and the nitrogen oxide contained in the test gas can be decomposed when a voltage equal to or higher than the second predetermined voltage is applied to the second electrode pair. Typically, it is desirable that the first electrode contains at least one selected from the group consisting of platinum (Pt), rhodium (Rh), and palladium (Pd).

As described above, the first electrode may be configured to be capable of decomposing the water and the sulfur oxide contained in the test gas when a voltage equal to or higher than the first predetermined voltage is applied to the first electrode pair. The first electrode that is capable of decomposing the water and the sulfur oxide at a predetermined applied voltage as described above can be produced by appropriately selecting, for example, the type of a substance constituting an electrode material and a heat treatment condition pertaining to the production of the electrode. Examples of the material constituting the first electrode include a substance (such as a precious metal) that has activity so that the water and the sulfur oxide contained in the test gas can be decomposed when a voltage equal to or higher than the first predetermined voltage is applied between the first electrode and the second electrode. Typically, it is desirable that the first electrode contains at least one selected from the group consisting of platinum (Pt), rhodium (Rh), and palladium (Pd).

The other objects, features, and additional advantages of the invention will become apparent in the following description of each embodiment of the invention based on accompanying drawings.

BRIEF DESCRIPTION OF THE DRAWINGS

Features, advantages, and technical and industrial significance of exemplary embodiments of the invention will be described below with reference to the accompanying drawings, in which like numerals denote like elements, and wherein.

DETAILED DESCRIPTION OF EMBODIMENTS

Hereinafter, a gas concentration detecting device according to a first embodiment of the invention (hereinafter, referred to as a "first device" in some cases) will be described.

Figure 1:
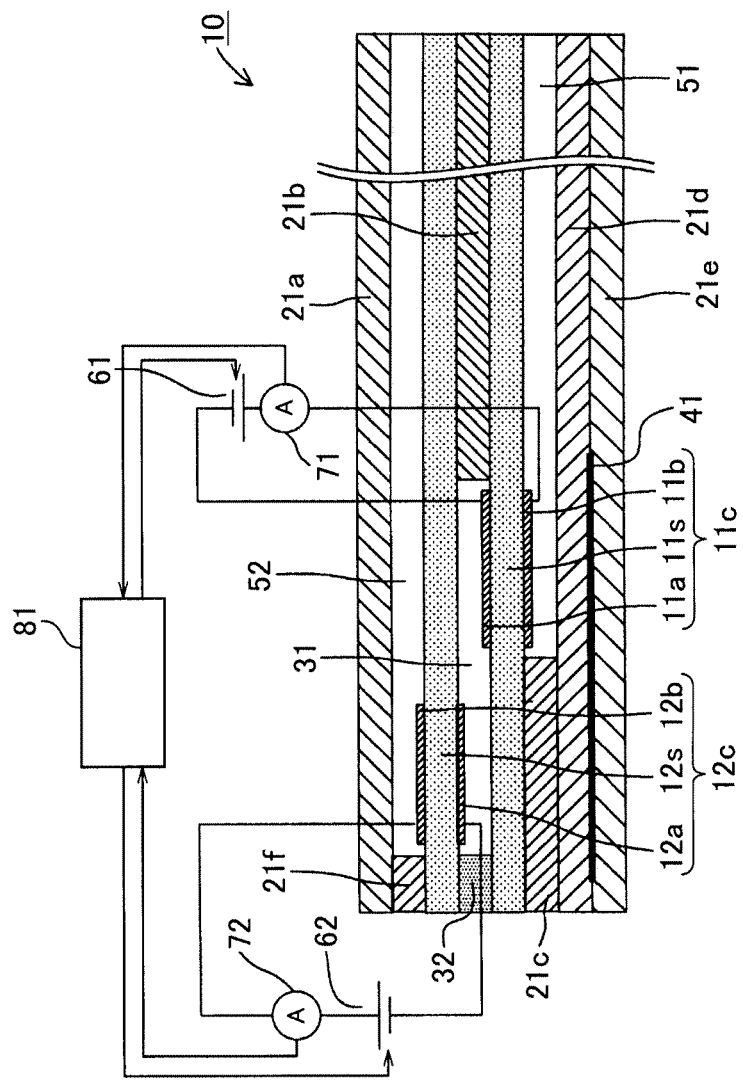
FIG. 1 is a schematic sectional view illustrating an example of the configuration of an element portion of a gas concentration detecting device (first device) according to a first embodiment of the invention.

As illustrated in FIG. 1, a gas concentration detecting element 10 of the first device is provided with a first solid electrolyte body 11s, a second solid electrolyte body 12s, a first alumina layer 21a, a second alumina layer 21b, a third alumina layer 21c, a fourth alumina layer 21d, a fifth alumina layer 21e, a sixth alumina layer 21f, a diffusion resistance unit (diffusion rate controlling layer) 32, and a heater 41. The first solid electrolyte body 11s is a sheet body that contains zirconia or the like and has oxide ion conductivity. The zirconia that forms the first solid electrolyte body 11s may contain an element such as scandium (Sc) and yttrium (Y) as is the case with the second solid electrolyte body 12s. The first to sixth alumina layers 21a to 21f are alumina-containing dense (gas-impermeable) layers (dense bodies). The diffusion resistance unit 32, which is a porous diffusion rate controlling layer, is a gas-permeable layer (sheet body). The heater 41 is a sheet body formed of cermet of, for example, platinum (Pt) and ceramics (such as alumina) The heater 41 is a heating element that generates heat when energized.

The respective layers of the gas concentration detecting element 10 are stacked in the order of the fifth alumina layer 21e, the fourth alumina layer 21d, the third alumina layer 21c, the first solid electrolyte body 11s, the diffusion resistance unit 32 and the second alumina layer 21b, the second solid electrolyte body 12s, the sixth alumina layer 21f, and the first alumina layer 21a from below.

An internal space 31 is a space that is defined by the first solid electrolyte body 11s, the second solid electrolyte body 12s, the diffusion resistance unit 32, and the second alumina layer 21b. Exhaust gas from an internal combustion engine is introduced, as test gas, into the internal space 31 via the diffusion resistance unit 32. In other words, the internal space 31 communicates with an inner portion of an exhaust pipe of the internal combustion engine (none of which is illustrated herein) via the diffusion resistance unit 32 in the gas concentration detecting element 10. Accordingly, the exhaust gas in the exhaust pipe is introduced into the internal space 31 as the test gas.

A first atmospheric air introduction path 51 is defined by the first solid electrolyte body 11$s$, the third alumina layer 21$c$, and the fourth alumina layer 21$d$ and is open toward the atmosphere outside the exhaust pipe. The first atmospheric air introduction path 51 corresponds to a first separate space. A second atmospheric air introduction path 52 is defined by the second solid electrolyte body 12$s$, the first alumina layer 21$a$, and the sixth alumina layer 21$f$ and is open toward the atmosphere outside the exhaust pipe. The second atmospheric air introduction path 52 corresponds to a second separate space.

A first electrode 11$a$ is a cathode and a second electrode 11$b$ is an anode. The first electrode 11$a$ is fixed to a surface on one side of the first solid electrolyte body 11$s$ (specifically, a surface of the first solid electrolyte body 11$s$ that defines the internal space 31). The second electrode 11$b$ is fixed to a surface on the other side of the first solid electrolyte body 11$s$ (specifically, a surface of the first solid electrolyte body 11$s$ that defines the first atmospheric air introduction path 51). The first electrode 11$a$, the second electrode 11$b$, and the first solid electrolyte body 11$s$ constitute a first electrochemical cell 11$c$ that is capable of oxygen pumping action-based oxygen discharge.

A third electrode 12$a$ is a cathode and a fourth electrode 12$b$ is an anode. The third electrode 12$a$ is fixed to a surface on one side of the second solid electrolyte body 12$s$ (specifically, a surface of the second solid electrolyte body 12$s$ that defines the internal space 31). The fourth electrode 12$b$ is fixed to a surface on the other side of the second solid electrolyte body 12$s$ (specifically, a surface of the second solid electrolyte body 12$s$ that defines the second atmospheric air introduction path 52). The third electrode 12$a$, the fourth electrode 12$b$, and the second solid electrolyte body 12$s$ constitute a second electrochemical cell 12$c$ that is capable of oxygen pumping action-based oxygen discharge. The first electrochemical cell 11$c$ and the second electrochemical cell 12$c$ are heated to an activation temperature by the heater 41.

The first solid electrolyte body 11$s$, the second solid electrolyte body 12$s$, and each of the first to sixth alumina layers 21$a$ to 21$f$ can be molded into a sheet shape by a doctor blade method, an extrusion molding method, or the like. The first electrode 11$a$, the second electrode 11$b$, the third electrode 12$a$, the fourth electrode 12$b$, and wiring or the like for the energization of the electrodes can be formed by a screen printing method or the like. When the sheets are stacked as described above and fired, the gas concentration detecting element 10 that has the above-described structure can be integrally produced.

The first electrode 11$a$ is a porous cermet electrode that contains an alloy of platinum (Pt) and rhodium (Rh) as a main component. The second electrode 11$b$ is a porous cermet electrode that contains platinum (Pt) as a main component. Likewise, the third electrode 12$a$ is a porous cermet electrode that contains an alloy of platinum (Pt) and rhodium (Rh) as a main component. The fourth electrode 12$b$ is a porous cermet electrode that contains platinum (Pt) as a main component.

In the example that is illustrated in FIG. 1, the second electrochemical cell 12$c$ includes the second solid electrolyte body 12$s$ that is separate from the first solid electrolyte body 11$s$ constituting the first electrochemical cell 11$c$. However, the second electrochemical cell 12$c$ may share the first solid electrolyte body 11$s$ with the first electrochemical cell 11$c$. In this case, the first atmospheric air introduction path 51 functions as the first separate space and the second separate space.

The first device is also provided with an electric power supply 61, an ammeter 71, and an ECU 81 (electronic control unit). The electric power supply 61 and the ammeter 71 are connected to the ECU 81. The electric power supply 61 can apply a predetermined voltage between the first electrode 11$a$ and the second electrode 11$b$ so that the potential of the second electrode 11$b$ exceeds the potential of the first electrode 11$a$. The operation of the electric power supply 61 is controlled by the ECU 81. The ammeter 71 measures the magnitude of an electrode current that is a current flowing between the first electrode 11$a$ and the second electrode 11$b$ (that is, a current flowing through the first solid electrolyte body 11$s$). The ammeter 71 outputs the measured value to the ECU 81.

The first device is also provided with an electric power supply 62 and an ammeter 72. The electric power supply 62 and the ammeter 72 are connected to the ECU 81. The electric power supply 62 can apply a predetermined voltage between the third electrode 12$a$ and the fourth electrode 12$b$ so that the potential of the fourth electrode 12$b$ exceeds the potential of the third electrode 12$a$. The operation of the electric power supply 62 is controlled by the ECU 81. The ammeter 72 measures the magnitude of an electrode current that is a current flowing between the third electrode 12$a$ and the fourth electrode 12$b$ (that is, a current flowing through the second solid electrolyte body 12$s$). The ammeter 72 outputs the measured value to the ECU 81.

The ECU 81 is configured as a microcomputer including a CPU, a ROM that stores a program, a map, and the like executed by the CPU, a RAM that temporarily stores data, and the like. The ECU 81 may be connected to actuators (not illustrated, examples including a fuel injection valve, a throttle valve, and an EGR valve) of the internal combustion engine. In this case, the ECU 81 sends driving (instruction) signals to the actuators and also controls the internal combustion engine.

The ECU 81 can control an applied voltage $Vm1$, which is applied to the first electrode 11$a$ and the second electrode 11$b$, by controlling the electric power supply 61. In addition, the ECU 81 can receive a signal correlated with an electrode current $Im1$ output from the ammeter 71 and flowing through the first electrochemical cell 11$c$. In addition, the ECU 81 can control an applied voltage $Vm2$, which is applied to the third electrode 12$a$ and the fourth electrode 12$b$, by controlling the electric power supply 62. In addition, the ECU 81 can receive a signal correlated with an electrode current $Im2$ output from the ammeter 72 and flowing through the second electrochemical cell 12$c$.

In the example that is illustrated in FIG. 1, the electric power supply 61 and the electric power supply 62 are included as separate electric power supplies. However, these electric power supplies may be configured as a single electric power supply insofar as intended applied voltages can be respectively applied between intended electrodes. In addition, a plurality of voltage control means may be configured to be connected in parallel to a single electric power source (such as a battery).

The concentrations of the oxygen and the nitrogen oxide contained in the exhaust gas discharged from the internal combustion engine can change in various ways depending on, for example, the air-fuel ratio and the combustion state of an air-fuel mixture combusted in a combustion chamber of the internal combustion engine. As a result, the concentrations of the oxygen and the nitrogen oxide contained in the test gas change in some cases. When the concentrations of the oxygen and the nitrogen oxide contained in the test gas change, the magnitude of the current flowing between the electrodes of the electrochemical cells capable of the oxygen pumping action also changes, and thus the accuracy of the detection of the concentration of a component whose concentration is to be detected (examples including water and sulfur oxide) may be reduced.

According to the gas concentration detecting element 10 of the first device, however, oxygen and nitrogen oxide can be discharged from the internal space 31 based on the oxygen pumping action when a first removing voltage is applied between the third electrode 12a and the fourth electrode 12b. More specifically, oxygen and nitrogen oxide are discharged from the internal space 31 to the second atmospheric air introduction path 52 when the first removing voltage is applied between the electrodes so that the third electrode 12a becomes a cathode and the fourth electrode 12b becomes an anode. In this manner, the oxygen and the nitrogen oxide that are contained in the test gas in the internal space 31 can be substantially removed by the second electrochemical cell 12c according to the gas concentration detecting element 10 of the first device.

In other words, according to the gas concentration detecting element 10 of the first device, oxygen and nitrogen oxide can be discharged from the internal space 31 based on the oxygen pumping action of the second electrochemical cell 12c as described above, and thus the concentrations of the oxygen and the nitrogen oxide in the internal space 31 can be adjusted to become constant (typically, at approximately 0 (zero) ppm) even when the concentrations of the oxygen and the nitrogen oxide contained in the test gas change.

When a measuring voltage is applied between the first electrode 11a and the second electrode 11b so that the potential of the second electrode 11b exceeds the potential of the first electrode 11a, not only the water contained in the test gas but also the sulfur oxide contained in the test gas is decomposed in the first electrode 11a. It is considered that the decomposition product of the sulfur oxide (examples including sulfur and a sulfur compound) adsorbs to the first electrode 11a and decreases the area of the first electrode 11a capable of contributing to the decomposition of water. As a result, a first detected value, which is correlated with the electrode current pertaining to the application of the measuring voltage between the first electrode 11a and the second electrode 11b, changes in accordance with the concentration of the sulfur oxide contained in the test gas.

When oxygen and/or nitrogen oxide are/is contained in the test gas reaching the first electrode 11a in this case, these components are also decomposed in the first electrode 11a. In other words, the first detected value is affected by the oxygen and/or nitrogen oxide contained in the test gas. According to the gas concentration detecting element 10, however, the oxygen and the nitrogen oxide contained in the test gas in the internal space 31 are substantially removed as described above by the second electrochemical cell 12c that is arranged on the upstream side of the first electrochemical cell 11c. Accordingly, in the first device, the effect on the electrode current Im1 detected in the first electrochemical cell 11c can be effectively reduced even when the concentrations of the oxygen and the nitrogen oxide contained in the test gas change. As a result, the concentration of the sulfur oxide contained in the test gas can be accurately detected with the first device.

Figure 2:
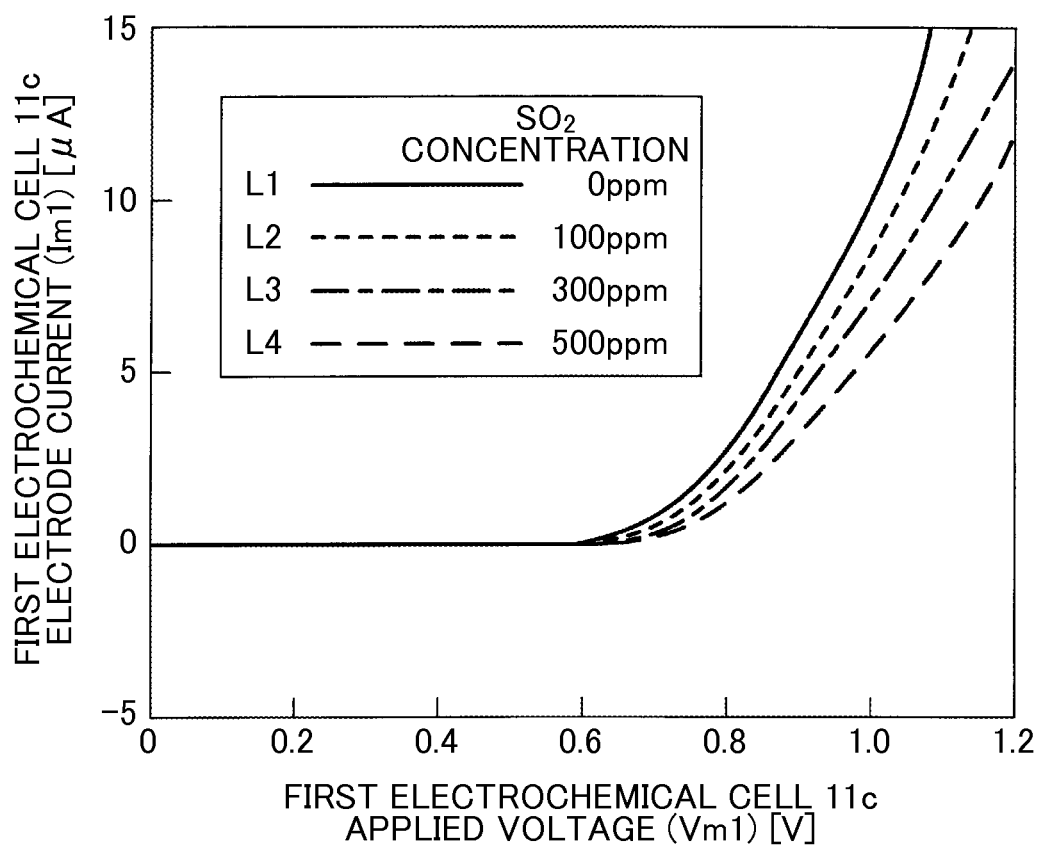
FIG. 2 is a schematic graph illustrating a relationship between a voltage (applied voltage) Vm1 that is applied between a first electrode and a second electrode which constitute a first electrochemical cell of the first device and an electrode current Im1 that flows between the electrodes.

A relationship between the applied voltage Vm1 and the electrode current Im1 regarding the first electrochemical cell 11c will be described in further detail. FIG. 2 is a schematic graph illustrating the relationship between the applied voltage Vm1 and the electrode current Im1 pertaining to a case where the applied voltage Vm1 is gradually raised (boost-swept) in the first electrochemical cell 11c. In this example, four different types of test gases are used, in which the concentrations of the sulfur dioxides ($SO_2$) as sulfur oxides contained in the test gases are 0 ppm, 100 ppm, 300 ppm, and 500 ppm. In addition, the concentrations of the oxygen and the nitrogen oxide contained in the test gas reaching the first electrode 11a (cathode) of the first electrochemical cell 11c is maintained to be constant (substantially at 0 (zero) ppm) for each of the test gases by the second electrochemical cell 12c arranged on the upstream side of the first electrochemical cell 11c.

The solid-line curve L1 shows the relationship between the applied voltage Vm1 and the electrode current Im1 pertaining to a case where the sulfur dioxide contained in the test gas has a concentration of 0 (zero) ppm. In the gas concentration detecting element 10, the oxygen and the nitrogen oxide contained in the test gas in the internal space 31 are substantially removed by the second electrochemical cell 12c as described above, and thus no electrode current flows (Im1=0 µA) in the region where the applied voltage Vm1 is lower than approximately 0.6 V. The electrode current Im1 begins to increase when the applied voltage Vm1 becomes equal to or higher than approximately 0.6 V. This increase in the electrode current Im1 is because water begins to be decomposed in the first electrode 11a.

The dotted-line curve L2 shows the relationship between the applied voltage Vm1 and the electrode current Im1 pertaining to a case where the sulfur dioxide contained in the test gas has a concentration of 100 ppm. The relationship between the applied voltage Vm1 and the electrode current Im1 pertaining to this case is similar to that shown by the curve L1 (case where the sulfur dioxide contained in the test gas has a concentration of 0 (zero) ppm) when the applied voltage Vm1 is lower than the voltage at which the decomposition of water begins in the first electrode 11a (decomposition initiation voltage) (approximately 0.6 V). In other words, the electrode current Im1 does not flow in the region where the applied voltage Vm1 is lower than approximately 0.6 V. When the applied voltage Vm1 is equal to or higher than the decomposition initiation voltage (approximately 0.6 V) of the water in the first electrode 11a, the decomposition of the water causes the electrode current Im1 to flow. However, the electrode current Im1 is lower than that of the curve L1 and the rate of increase in the electrode current Im1 with respect to the applied voltage Vm1 is also lower than that of the curve L1 (gentler slope).

The curve L3 that is shown by the one-dot chain line shows the relationship between the applied voltage Vm1 and the electrode current Im1 pertaining to a case where the sulfur dioxide contained in the test gas has a concentration of 300 ppm. The dashed-line curve L4 shows the relationship between the applied voltage Vm1 and the electrode current Im1 pertaining to a case where the sulfur dioxide contained in the test gas has a concentration of 500 ppm. In both cases, the electrode current Im1 does not flow when the applied voltage Vm1 is lower than the decomposition initiation voltage (approximately 0.6 V) of the water in the first electrode 11a. The electrode current Im1 flows, because of the decomposition of the water, when the applied voltage Vm1 is equal to or higher than the decomposition initiation voltage (approximately 0.6 V) of the water in the first electrode 11a. However, the electrode current Im1 decreases as the concentration of the sulfur dioxide contained in the test gas increases, and the rate of increase in the electrode current Im1 with respect to the applied voltage Vm1 also decreases as the concentration of the sulfur dioxide contained in the test gas increases (gentler slope).

Figure 3:
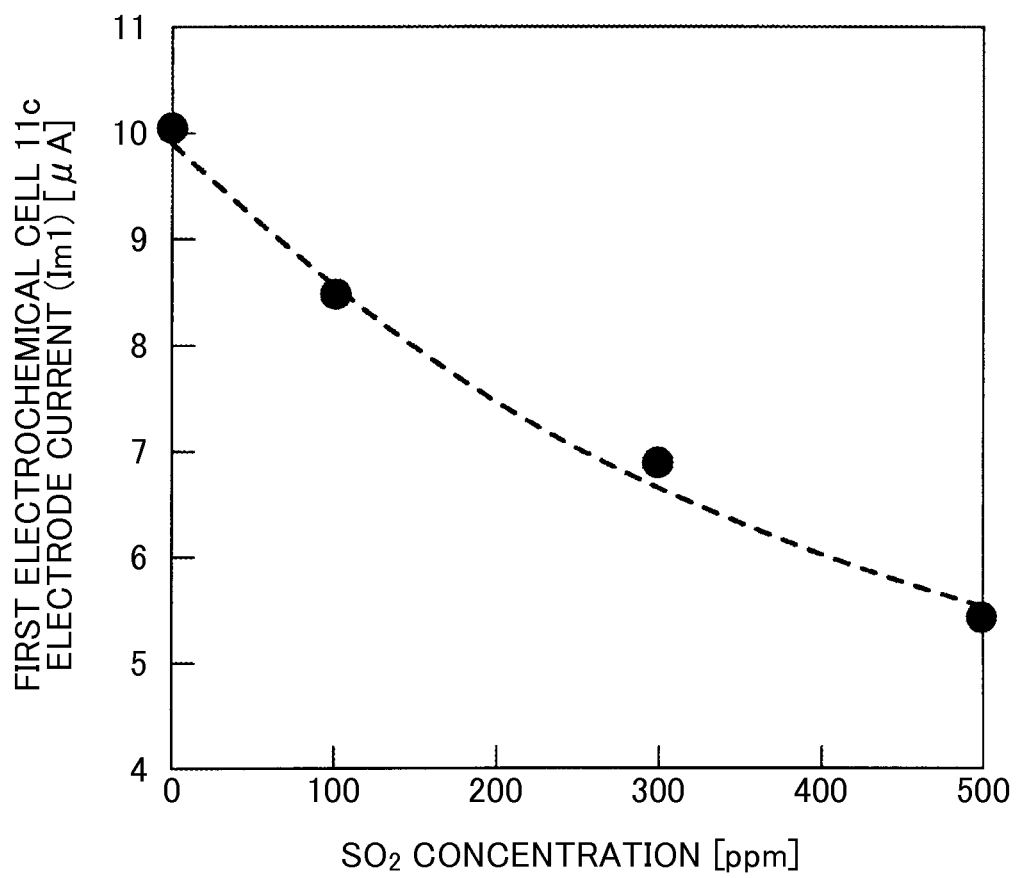
FIG. 3 is a schematic graph illustrating a relationship between the magnitude of the electrode current Im1 and the concentration of sulfur dioxide ($SO_2$) contained in test gas pertaining to a case where the applied voltage Vm1 is 1.0 V in the first device.

As described above, the magnitude of the electrode current Im1 pertaining to a case where the applied voltage Vm1 is equal to or higher than the decomposition initiation voltage (approximately 0.6 V) of the water in the first electrode 11a changes in accordance with the concentration of the sulfur dioxide as the sulfur oxide contained in the test gas. The graph that is illustrated in FIG. 3 is obtained when, for example, the magnitude of the electrode current Im1 according to the curves L1 to L4 pertaining to a case where the applied voltage Vm1 is 1.0 V in the graph illustrated in FIG. 2 is plotted with respect to the concentration of the sulfur dioxide contained in the test gas. As shown by the dotted-line curve in FIG. 3, the magnitude of the electrode current Im1 at a specific applied voltage Vm1 (1.0 V in this case) changes in accordance with the concentration of the sulfur dioxide contained in the test gas. Accordingly, when (the first detected value correlated with) the electrode current Im1 at a specific applied voltage Vm1 (which is a predetermined voltage equal to or higher than the decomposition initiation voltage of the water and is also referred to as a "first predetermined voltage") is acquired, the concentration of the sulfur oxide correlated with the electrode current Im1 (correlated with the first detected value) can be acquired.

The respective specific values of the applied voltage Vm1 shown on the horizontal axis of the graph illustrated in FIG. 2, the electrode current Im1 shown on the vertical axis of the graph illustrated in FIG. 2, and the applied voltage Vm1 described above may change in accordance with the conditions (examples including the concentrations of various components contained in the test gas) of an experiment performed so as to obtain the graph illustrated in FIG. 2, and the values of the applied voltage Vm1 and the electrode current Im1 are not always limited to the values described above.

Figure 4:
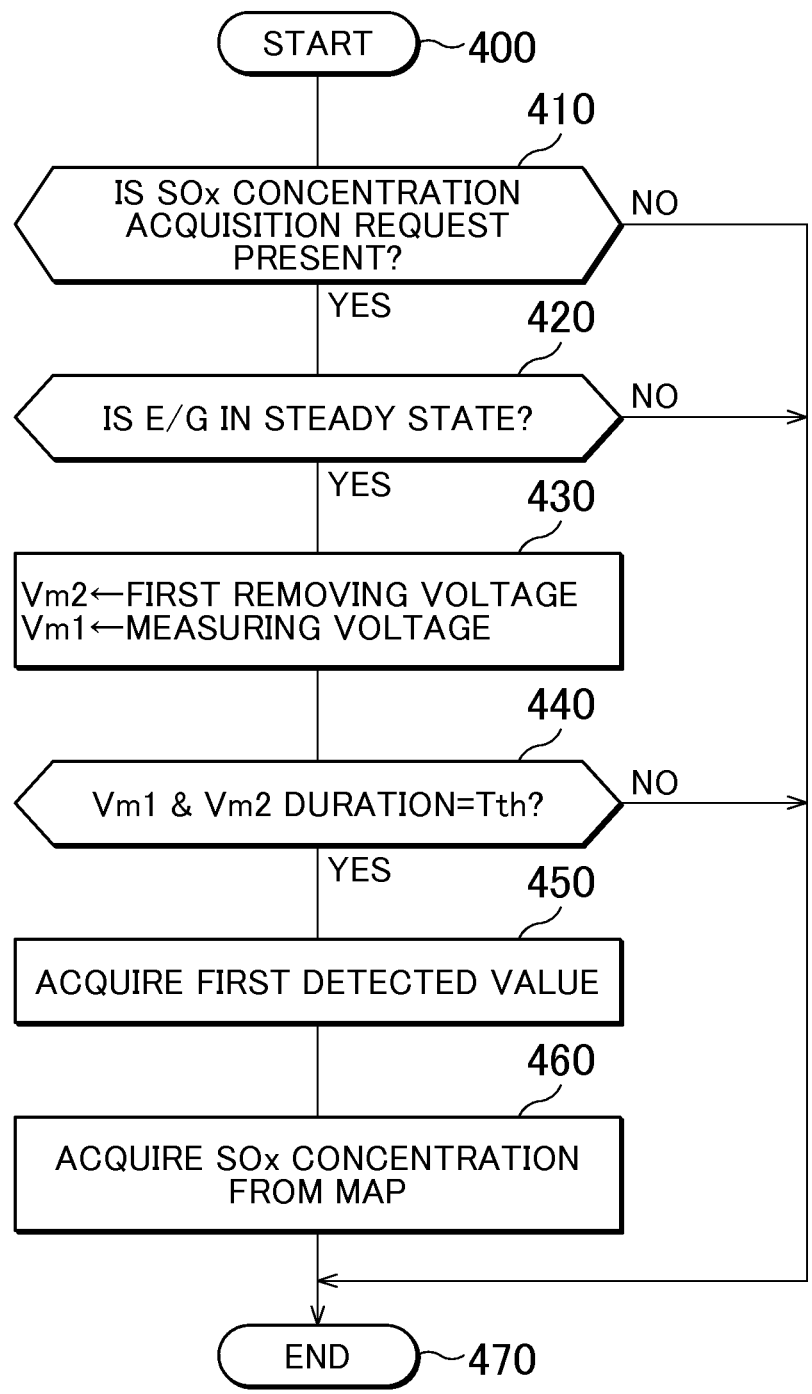
FIG. 4 is a flowchart illustrating the "SOx concentration acquisition processing routine" that is executed by an acquisition unit of the first device.

The SOx concentration acquisition processing routine that is executed in the first device will be described in further detail. FIG. 4 is a flowchart illustrating the "SOx concentration acquisition processing routine" that the ECU 81 executes by using the gas concentration detecting element 10. For example, the CPU of the ECU 81 described above (hereinafter, simply referred to as the "CPU" in some cases) initiates the processing at a predetermined timing and allows the processing to proceed from Step 400 to Step 410.

Firstly, in Step 410, the CPU determines whether or not a request for the acquisition of the concentration of the sulfur oxide contained in the test gas (SOx concentration acquisition request) is present. The SOx concentration acquisition request is generated when, for example, a fuel tank is filled with fuel in a vehicle on which the internal combustion engine to which the first device is applied is mounted. The SOx concentration acquisition request may be released in a case where the SOx concentration acquisition processing routine is executed after the fuel tank is filled with the fuel and a history of the acquisition of the concentration of the sulfur oxide contained in the test gas is present.

In a case where it is determined in Step 410 that the SOx concentration acquisition request is present (Step 410: Yes), the CPU allows the processing to proceed to Step 420 and determines whether or not the internal combustion engine (E/G) to which the first device is applied is in a steady state. The CPU determines that the internal combustion engine is in the steady state when, for example, the difference between the maximum value and the minimum value of a load within a predetermined period of time is lower than a threshold or when the difference between the maximum value and the minimum value of an accelerator operation amount within a predetermined period of time is lower than a threshold.

In a case where it is determined in Step 420 that the internal combustion engine is in the steady state (Step 420: Yes), the CPU allows the processing to proceed to Step 430 and applies the first removing voltage (0.4 V in the first device) between the third electrode 12a and the fourth electrode 12b as the applied voltage Vm2 while applying the measuring voltage (1.0 V in the first device) between the first electrode 11a and the second electrode 11b as the applied voltage Vm1.

Then, the CPU allows the processing to proceed to Step 440 and determines whether or not the duration of the period when the measuring voltage as the applied voltage Vm1 and the first removing voltage as the applied voltage Vm2 are applied corresponds to a predetermined threshold (Tth). This threshold Tth corresponds to the length of a period that is sufficient for the decomposition product to adsorb to the first electrode 11a, which is a cathode, and reduce the electrode current with the sulfur oxide contained in the test gas decomposed by the applied voltage Vm1 between the first electrode 11a and the second electrode 11b becoming the first predetermined voltage. A specific value of the threshold Tth (length of time) can be determined based on, for example, a prior experiment in which the gas concentration detecting element 10 of the first device is used.

In a case where it is determined in Step 440 that the duration of the period corresponds to the predetermined threshold (Step 440: Yes), the CPU allows the processing to proceed to Step 450 and acquires the electrode current Im1 as the first detected value. Then, the CPU allows the processing to proceed to Step 460 and acquires the concentration of the sulfur oxide correlated with the first detected value by, for example, referring to the data map that is illustrated in FIG. 3. Then, the CPU allows the processing to proceed to Step 470 and terminates the routine. In this manner, the first device can accurately detect the concentration of the sulfur oxide contained in the test gas.

In a case where it is determined in Step 410 that the SOx concentration acquisition request is absent (Step 410: No), in a case where it is determined in Step 420 that the internal combustion engine is not in the steady state (Step 420: No), or in a case where it is determined in Step 440 that the duration does not correspond to the predetermined threshold (Tth) (Step 440: No), the CPU allows the processing to proceed to Step 470 and terminates the routine.

A program that allows the routine described above to be executed by the CPU can be stored in a data storage device (such as the ROM) of the ECU 81. In addition, a correspondence relationship between the electrode current Im1 as the first detected value and the concentration of the sulfur oxide contained in the test gas pertaining to a case where the applied voltage Vm1 is the measuring voltage (1.0 V in the first device) can be obtained in advance in, for example, a prior experiment using test gas with a known sulfur oxide concentration. A data table (such as a data map) showing the correspondence relationship can be stored in the data storage device (such as the ROM) of the ECU 81 so that the CPU can refer to the data table in Step 460.

In the first device, the first removing voltage is 0.4 V as described above. However, the first removing voltage is not particularly limited insofar as the first removing voltage is equal to or higher than the lower limit of the voltage range where the limiting current characteristics of the nitrogen oxide are expressed and is a predetermined voltage which is lower than the voltage at which the decomposition of the sulfur oxide is initiated in the case of application between the third electrode 12a and the fourth electrode 12b with the third electrode 12a being a cathode and the fourth electrode 12b being an anode as described above. The limiting current region of the nitrogen oxide is approximately 0.1 V to at least 0.2 V and the voltage at which the decomposition of the sulfur oxide is initiated is approximately 0.5 V to 0.6 V. In this voltage range, the limiting current characteristics of oxygen are also expressed.

The limiting current region of the nitrogen oxide described above tends to shift to a high voltage side as the concentration of the oxygen contained in the test gas increases. Accordingly, it is desirable that a second voltage application unit is configured for the first removing voltage to increase as the concentration of the oxygen contained in the test gas increases.

The measuring voltage is 1.0 V in the first device. However, the measuring voltage is not particularly limited insofar as the measuring voltage is a predetermined voltage that allows the decomposition of the water and the sulfur oxide contained in the test gas when applied between the first electrode 11a and the second electrode 11b with the first electrode 11a being a cathode and the second electrode 11b being an anode as described above. The voltage at which the decomposition of the water is initiated is approximately 0.6 V as described above. Accordingly, it is desirable that the measuring voltage is a predetermined voltage of at least 0.6 V.

When the applied voltage Vm1 is a voltage equal to or higher than the lower limit voltage of the limiting current region of the water, the rate of supply of the water reaching the first electrode (cathode) via the diffusion resistance unit is lower than the rate of decomposition of the water in the first electrode. In other words, the limiting current characteristics of the water are expressed. In this case, it may be difficult to accurately detect the concentration of the sulfur oxide contained in the test gas based on the first detected value. In addition, an excessive increase in the applied voltage Vm1 may result in the decomposition of another component contained in the test gas (such as carbon dioxide ($CO_2$)) and/or the first solid electrolyte body 11s. Accordingly, it is desirable that the measuring voltage is a predetermined voltage lower than the lower limit voltage of the limiting current region of the water. In other words, it is desirable that the measuring voltage is equal to or higher than the voltage at which the decomposition of the water is initiated and is a predetermined voltage lower than the lower limit of the voltage range in which the limiting current characteristics of the water are expressed (observed). The lower limit voltage of the limiting current region of the water is approximately 2.0 V although slight fluctuations are seen depending on, for example, the concentration of the water contained in the test gas and measurement conditions.

In the first device, the magnitude of the electrode current flowing between the first electrode 11a and the second electrode 11b when the measuring voltage is applied between the first electrode 11a and the second electrode 11b is the first detected value. However, the first detected value is not particularly limited insofar as the first detected value is the value of any signal correlated with the electrode current (examples including a voltage value, a current value, and a resistance value) as described above. In a case where the value of a signal that has a positive correlation with the electrode current (such as a voltage value and a current value) is adopted as the first detected value, the first device is configured to detect a higher SOx concentration value as the first detected value decreases. In a case where the value of a signal that has a negative correlation with the electrode current is adopted as the first detected value, the first device is configured to detect a higher SOx concentration value as the first detected value increases.

In the first device, the third electrode 12a is a porous cermet electrode that contains an alloy of platinum (Pt) and rhodium (Rh) as a main component and the fourth electrode 12b is a porous cermet electrode that contains platinum (Pt) as a main component. However, the material that constitutes the third electrode 12a is not particularly limited insofar as reductive decomposition can be performed on the oxygen and the nitrogen oxide contained in the test gas introduced into the internal space 31 via the diffusion resistance unit 32 when a second predetermined voltage is applied between the third electrode 12a and the fourth electrode 12b. Preferably, the material that constitutes the third electrode 12a contains, as a main component, a platinum group element such as platinum (Pt), rhodium (Rh), and palladium (Pd) or an alloy thereof. More preferably, the third electrode 12a is a porous cermet electrode that contains, as a main component, at least one selected from the group consisting of platinum (Pt), rhodium (Rh), and palladium (Pd).

Likewise, in the first device, the first electrode 11a is a porous cermet electrode that contains an alloy of platinum (Pt) and rhodium (Rh) as a main component and the second electrode 11b is a porous cermet electrode that contains platinum (Pt) as a main component. However, the material that constitutes the first electrode 11a is not particularly limited insofar as reductive decomposition can be performed on the water and the sulfur oxide contained in the test gas introduced into the internal space 31 via the diffusion resistance unit 32 when the first predetermined voltage is applied between the first electrode 11a and the second electrode 11b. Preferably, the material that constitutes the first electrode 11a contains, as a main component, a platinum group element such as platinum (Pt), rhodium (Rh), and palladium (Pd) or an alloy thereof. More preferably, the first electrode 11a is a porous cermet electrode that contains, as a main component, at least one selected from the group consisting of platinum (Pt), rhodium (Rh), and palladium (Pd).

Hereinafter, a gas concentration detecting device according to a second embodiment of the invention (hereinafter, referred to as a "second device" in some cases) will be described.

A gas concentration detecting element 20 of the second device is similar in configuration to the gas concentration detecting element 10 of the first device with the only exception that a third electrochemical cell 13c, which is arranged on the upstream side of the second electrochemical cell 12c (diffusion resistance unit 32 side), is further provided. The following description of the configuration of the second device will focus on how the second device differs from the first device.

Figure 5:
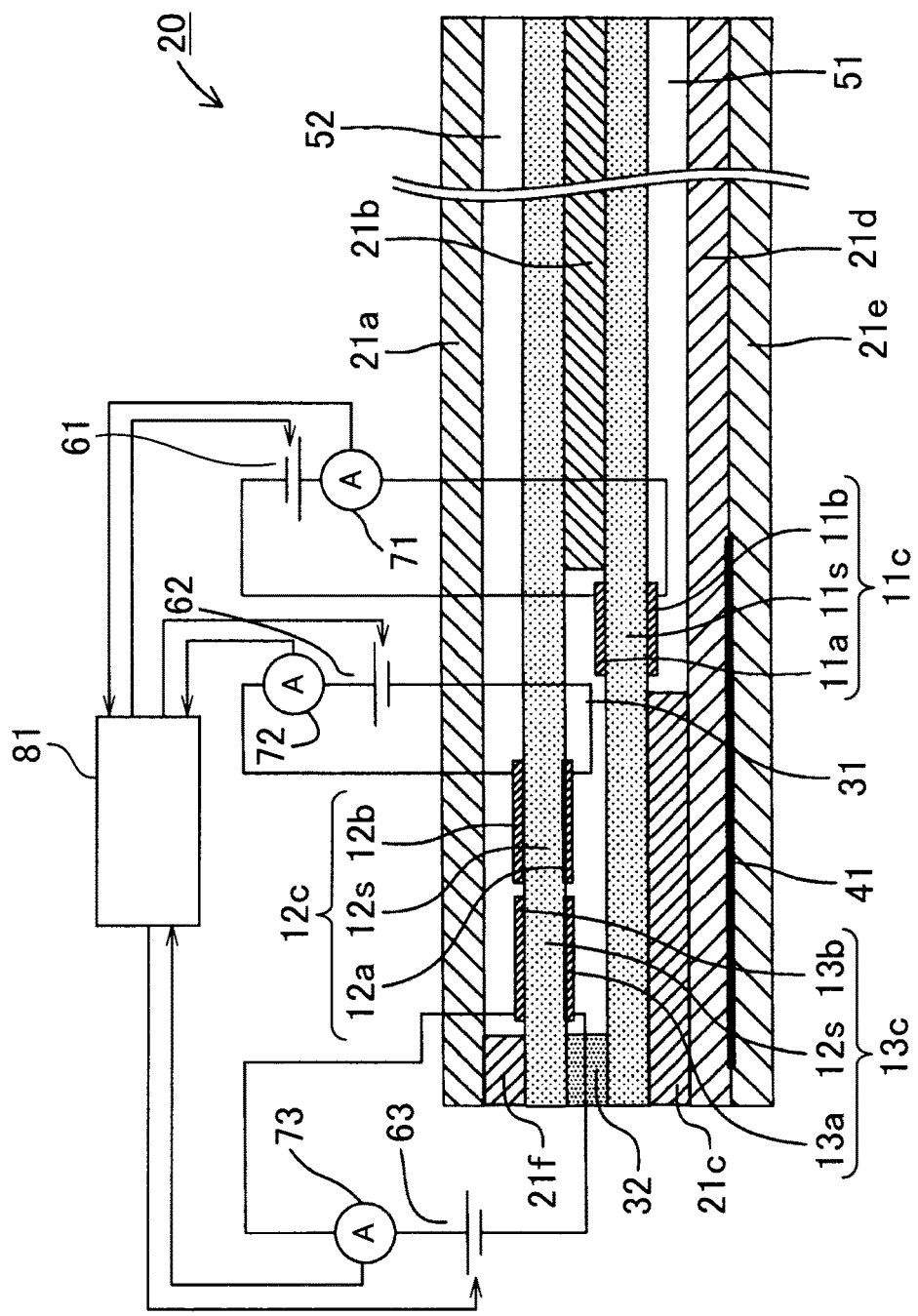
FIG. 5 is a schematic sectional view illustrating an example of the configuration of an element portion of a gas concentration detecting device (second device) according to a second embodiment of the invention.

As illustrated in FIG. 5, a fifth electrode 13a, a sixth electrode 13b, and the second solid electrolyte body 12s constitute the third electrochemical cell 13c and the third electrochemical cell 13c is arranged on the upstream side of the second electrochemical cell 12c (diffusion resistance unit 32 side) in the gas concentration detecting element 20. The fifth electrode 13a is a cathode and the sixth electrode 13b is an anode. The fifth electrode 13a is fixed to a surface on one side of the second solid electrolyte body 12s (specifically, a surface of the second solid electrolyte body 12s that defines the internal space 31). The sixth electrode 13b is fixed to a surface on the other side of the second solid electrolyte body 12s (specifically, a surface of the second solid electrolyte body 12s that defines the second atmospheric air introduction path 52). The fifth electrode 13a is arranged to face the internal space 31 at a position closer to the diffusion resistance unit 32 than the third electrode 12a is.

An electric power supply 63 can apply a predetermined voltage between the fifth electrode 13a and the sixth electrode 13b so that the potential of the sixth electrode 13b exceeds the potential of the fifth electrode 13a. The operation of the electric power supply 63 is controlled by the ECU 81. The ECU 81 can control an applied voltage Vm3 that is applied to the fifth electrode 13a and the sixth electrode 13b. In the second device, both a second removing voltage and the first removing voltage are 0.4 V.

An ammeter 73 measures the magnitude of an electrode current Im3 that is a current flowing between the fifth electrode 13a and the sixth electrode 13b (that is, a current flowing through the second solid electrolyte body 12s). The ammeter 73 outputs the measured value to the ECU 81. The ECU 81 can receive a signal correlated with the electrode current Im3 output from the ammeter 73 and flowing through the third electrochemical cell 13c.

The third electrode 12a is a porous cermet electrode that contains an alloy of platinum (Pt) and rhodium (Rh) as a main component. The fourth electrode 12b is a porous cermet electrode that contains platinum (Pt) as a main component. The fifth electrode 13a is a porous cermet electrode that contains an alloy of platinum (Pt) and gold (Au) as a main component. The sixth electrode 13b is a porous cermet electrode that contains platinum (Pt) as a main component. In other words, the fifth electrode 13a itself is produced for nitrogen oxide not to be substantially decomposed, despite oxygen decomposition, even at a predetermined applied voltage.

As described above, the third electrochemical cell 13c allows only the oxygen decomposition, without allowing any substantial decomposition of the nitrogen oxide contained in the test gas, despite the application of the applied voltage Vm3 (0.4 V) equal to the applied voltage Vm2 of the second electrochemical cell 12c. In other words, the electrode current Im3 of the third electrochemical cell includes only the current attributable to the oxygen decomposition without substantially including any current attributable to the decomposition of the nitrogen oxide. The second electrochemical cell 12c is arranged on the downstream side of the third electrochemical cell 13c. The oxygen contained in the test gas is removed by the third electrochemical cell and the second electrochemical cell 12c decomposes only the nitrogen oxide. In other words, the electrode current Im2 of the second electrochemical cell includes only the current attributable to the decomposition of the nitrogen oxide without substantially including any current attributable to the oxygen decomposition.

Accordingly, with the second device, the concentration of the oxygen contained in the test gas can be detected based on a third detected value correlated with the electrode current Im3 of the third electrochemical cell 13c. In addition, the concentration of the nitrogen oxide contained in the test gas can be detected based on a second detected value correlated with the electrode current Im2 of the second electrochemical cell 12c. Specifically, the second device can individually detect the concentrations of the oxygen and the nitrogen oxide contained in the test gas based on the electrode current Im3 (third detected value) pertaining to a case where the second removing voltage (applied voltage Vm3=0.4 V) is applied between the fifth electrode 13a and the sixth electrode 13b of the third electrochemical cell 13c and the electrode current Im2 (second detected value) pertaining to a case where the first removing voltage (applied voltage Vm2=0.4 V) is applied between the third electrode 12a and the fourth electrode 12b of the second electrochemical cell 12c, respectively.

According to the gas concentration detecting element 20, oxygen is discharged from the internal space 31 based on an oxygen pumping action when the second removing voltage is applied between the fifth electrode 13a and the sixth electrode 13b with the fifth electrode 13a being a cathode and the sixth electrode 13b being an anode. In addition, nitrogen oxide is discharged from the internal space 31 based on an oxygen pumping action when the first removing voltage is applied between the third electrode 12a and the fourth electrode 12b with the third electrode 12a being a cathode and the fourth electrode 12b being an anode. In this manner, the oxygen and the nitrogen oxide in the internal space 31 are removed by the third electrochemical cell 13c and the second electrochemical cell 12c in the gas concentration detecting element 20. Accordingly, the test gas reaching the first electrode 11a (cathode) of the first electrochemical cell 11c contains substantially no oxygen or nitrogen oxide according to the gas concentration detecting element 20.

In other words, according to the gas concentration detecting element 20, the effect on the electrode current Im1 detected in the first electrochemical cell 11c can be effectively reduced even when the concentrations of the oxygen and the nitrogen oxide contained in the test gas change. As a result, the concentration of the sulfur oxide contained in the test gas can be accurately detected with the second device.

In the example that is illustrated in FIG. 5, the third electrochemical cell 13c and the second electrochemical cell 12c are configured to share the second solid electrolyte body 12s. In this case, the second atmospheric air introduction path 52 functions as the second separate space and a third separate space. However, the third electrochemical cell 13c and the second electrochemical cell 12c may be configured to include separate solid electrolytes. In the example that is illustrated in FIG. 5, the third electrochemical cell 13c and the second electrochemical cell 12c include the second solid electrolyte body 12s separate from the first solid electrolyte body 11s that constitutes the first electrochemical cell 11c. However, any one or both of the third electrochemical cell 13c and the second electrochemical cell 12c may share the first solid electrolyte body 11s with the first electrochemical cell 11c. In this case, the first atmospheric air introduction path 51 functions as not only the first separate space but also any one or both of the third separate space and the second separate space.

Hereinafter, a gas concentration detecting device according to a third embodiment of the invention (hereinafter, referred to as a "third device" in some cases) will be described.

Figure 6A:
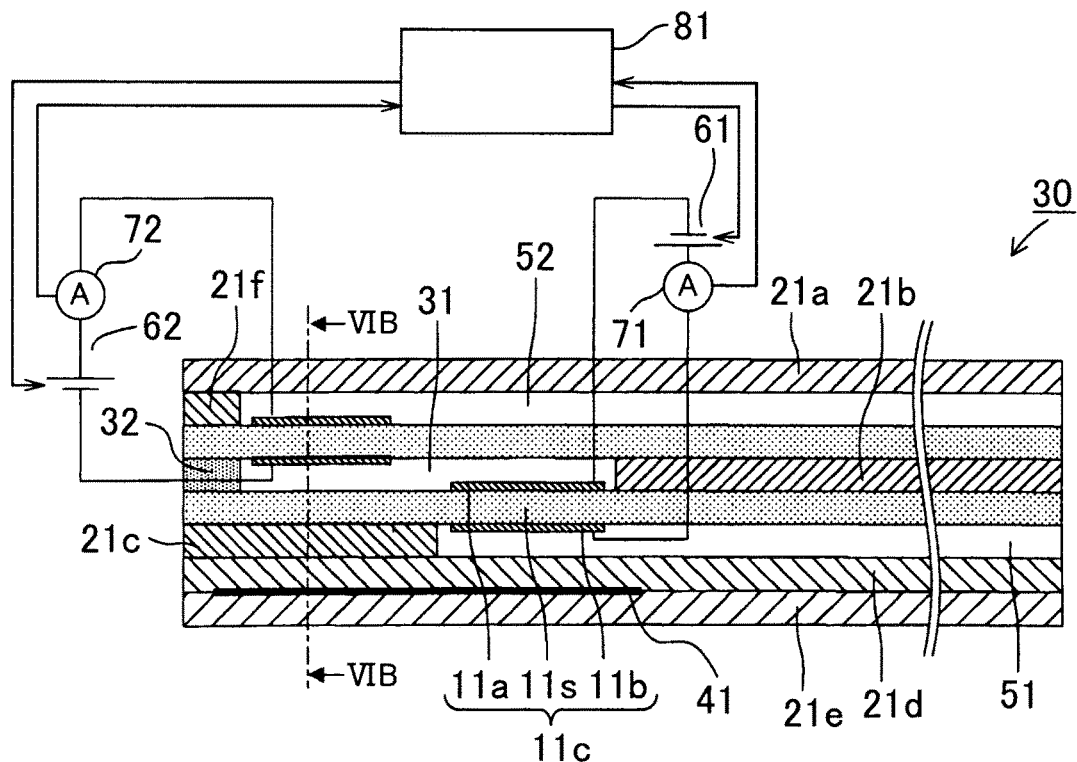
FIG. 6A is a schematic sectional view illustrating an example of the configuration of an element portion of a gas concentration detecting device (third device) according to a third embodiment of the invention.
Figure 6B:
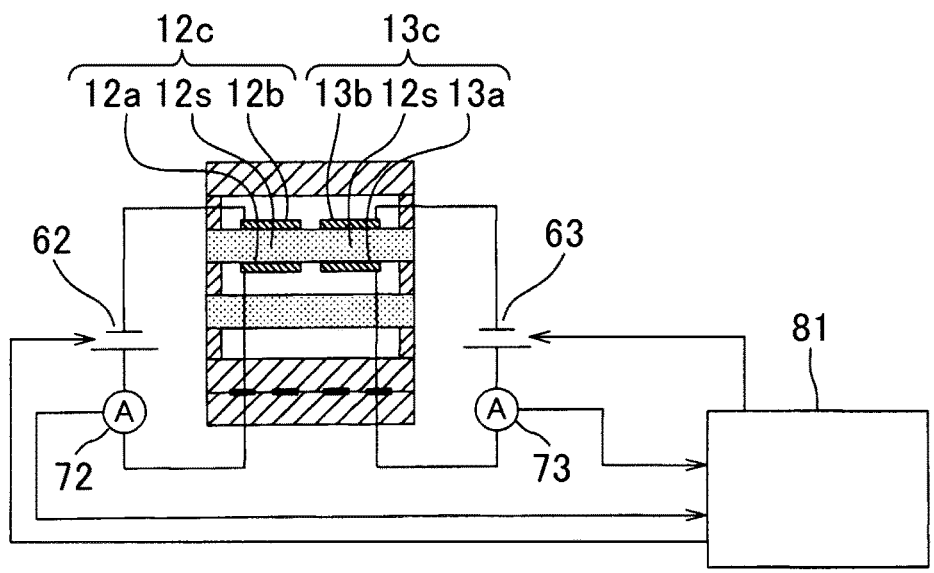
FIG. 6B is a schematic sectional view, taken along line VIB-VIB in FIG. 6A, illustrating the example of the configuration of the element portion of the gas concentration detecting device (third device) according to the third embodiment of the invention.

As illustrated in FIGS. 6A and 6B, a gas concentration detecting element 30 of the third device is similar in configuration to the gas concentration detecting element 20 of the second device with the only exception that the third electrochemical cell 13c and the second electrochemical cell 12c are arranged in parallel to each other and in the vicinity of each other instead of being arranged (in series) on the upstream side and the downstream side in the internal space 31, respectively. Herein, the "vicinity" refers to a region reached by test gas containing oxygen with the concentration equal to the concentration of the oxygen contained in the test gas reaching the cathodes of these electrochemical cells. The following description of the configuration of the third device will focus on how the third device differs from the second device.

FIG. 6B is a sectional view of the gas concentration detecting element 30 taken along line VIB-VIB in FIG. 6A.

In the example of the third device that is illustrated in FIG. 6B, the third electrochemical cell 13c and the second electrochemical cell 12c are disposed side by side in the vicinity of each other. Specifically, the third electrochemical cell 13c and the second electrochemical cell 12c of the third device are arranged, in the internal space 31, at positions away to the downstream side by the same distance from the diffusion resistance unit 32.

The third electrochemical cell 13c shares the second solid electrolyte body 12s with the second electrochemical cell 12c and has the fifth electrode 13a and the sixth electrode 13b, which are a pair of electrodes arranged on surfaces of the third electrochemical cell 13c. In the third device, the fifth electrode 13a is arranged to face the internal space 31 and the sixth electrode 13b is arranged to face the second atmospheric air introduction path 52.

The electric power supply 63 applies the applied voltage Vm3 between the fifth electrode 13a and the sixth electrode 13b so that the potential of the sixth electrode 13b exceeds the potential of the fifth electrode 13a. The ammeter 73 outputs, to the ECU 81, a signal correlated with the electrode current Im3 flowing through the third electrochemical cell 13c. The ECU 81 can control the applied voltage that is applied to the fifth electrode 13a and the sixth electrode 13b. In the third device, both the second removing voltage and the first removing voltage are 0.4 V. The ECU 81 can receive a signal correlated with the electrode current Im3 output from the ammeter 73 and flowing through the third electrochemical cell 13c. The ECU 81 can receive a signal correlated with the electrode current Im2 output from the ammeter 72 and flowing through the second electrochemical cell 12c. Accordingly, the ECU 81 can detect the difference between the electrode current Im2 flowing through the second electrochemical cell 12c and the electrode current Im3 flowing through the third electrochemical cell 13c.

As in the second device, the third electrode 12a is a porous cermet electrode that contains an alloy of platinum (Pt) and rhodium (Rh) as a main component and the fourth electrode 12b is a porous cermet electrode that contains platinum (Pt) as a main component. The fifth electrode 13a is a porous cermet electrode that contains an alloy of platinum (Pt) and gold (Au) as a main component. The sixth electrode 13b is a porous cermet electrode that contains platinum (Pt) as a main component. In other words, the fifth electrode 13a itself is produced for nitrogen oxide not to be substantially decomposed, despite oxygen decomposition, even at a predetermined applied voltage.

As described above, the third electrochemical cell 13c allows only the oxygen decomposition, without allowing any substantial decomposition of the nitrogen oxide contained in the test gas, despite the application of the applied voltage Vm3 (0.4 V) equal to the applied voltage Vm2 of the second electrochemical cell 12c. In other words, the electrode current Im3 of the third electrochemical cell includes only the current attributable to the oxygen decomposition without substantially including any current attributable to the decomposition of the nitrogen oxide. The second electrochemical cell 12c decomposes both the oxygen and the nitrogen oxide contained in the test gas despite the application of the applied voltage equal to that of the third electrochemical cell 13c. In other words, the electrode current Im2 of the second electrochemical cell includes both the current attributable to the oxygen decomposition and the current attributable to the decomposition of the nitrogen oxide. Accordingly, the concentration of the nitrogen oxide contained in the test gas can be detected based on the difference between the third detected value correlated with the electrode current Im3 of the third electrochemical cell 13c and the second detected value correlated with the electrode current Im2 of the second electrochemical cell 12c.

Specifically, the third device can accurately detect the concentration of the oxygen contained in the test gas based on the electrode current Im3 (third detected value) pertaining to a case where the second removing voltage (applied voltage Vm3=0.4 V) is applied between the fifth electrode 13a and the sixth electrode 13b of the third electrochemical cell 13c. In addition, the ECU 81 can detect the difference between the electrode current Im2 (second detected value) and the electrode current Im3 (third detected value) pertaining to a case where the first removing voltage (applied voltage Vm2=0.4 V) is applied between the third electrode 12a and the fourth electrode 12b of the second electrochemical cell 12c and accurately detect the concentration of the nitrogen oxide contained in the test gas based on the detected difference. In this manner, the third device can individually detect the concentrations of the oxygen and the nitrogen oxide contained in the test gas.

In the gas concentration detecting element 30, the oxygen and the nitrogen oxide in the internal space 31 are removed by the third electrochemical cell 13c and the second electrochemical cell 12c as described above. Accordingly, the test gas reaching the first electrode 11a (cathode) of the first electrochemical cell 11c contains substantially no oxygen or nitrogen oxide according to the gas concentration detecting element 30.

In other words, according to the gas concentration detecting element 30, the effect on the electrode current Im1 detected in the first electrochemical cell 11c can be effectively reduced even when the concentrations of the oxygen and the nitrogen oxide contained in the test gas change. As a result, the concentration of the sulfur oxide contained in the test gas can be accurately detected with the third device.

In the example that is illustrated in FIG. 6, the third electrochemical cell 13c shares the second solid electrolyte body 12s with the second electrochemical cell 12c. However, the third electrochemical cell 13c and the second electrochemical cell 12c may include separate solid electrolyte bodies.

In the example that is illustrated in FIG. 6, the third electrochemical cell 13c and the second electrochemical cell 12c are arranged in the vicinity of each other. However, the positional relationship of these electrochemical cells are not particularly limited insofar as the condition is satisfied that the concentration of the oxygen contained in the test gas reaching the fifth electrode 13a as the cathode of the third electrochemical cell 13c is equal to the concentration of the oxygen contained in the test gas reaching the third electrode 12a as the cathode of the second electrochemical cell 12c.

Several embodiments and modification examples that have specific configurations have been described with reference to the accompanying drawings for the description of the invention. However, the scope of the invention is not limited to the exemplary embodiments and modification examples, and appropriate changes can be added thereto without departing from the scope of claims and the specification.

What is claimed is:

1. A gas concentration detecting device comprising:
a gas concentration detecting element including a first electrochemical cell, a second electrochemical cell, a dense body, and a diffusion resistance unit, the first electrochemical cell including a first solid electrolyte body, a first electrode, and a second electrode, the first solid electrolyte body having oxide ion conductivity, the first electrode and the second electrode being arranged on respective surfaces of the first solid electrolyte body, the second electrochemical cell including a second solid electrolyte body, a third electrode and a fourth electrode, the second solid electrolyte body having oxide ion conductivity, the third electrode and the fourth electrode being arranged on respective surfaces of the second solid electrolyte body, the first solid electrolyte body, the second solid electrolyte body, the dense body and the diffusion resistance unit being configured to define an internal space, the diffusion resistance unit being configured to introduce exhaust gas from an internal combustion engine as test gas into the internal space via the diffusion resistance unit, the first electrode being exposed to the internal space, the second electrode being exposed to a first atmospheric air introduction path, which is apart from the internal space, the third electrode being arranged at a position in the internal space closer to the diffusion resistance unit than the first electrode is, the fourth electrode being exposed to a second atmospheric air introduction path, which is apart from the internal space, the first electrode being configured to decompose water and sulfur oxide contained in the test gas when a voltage equal to or higher than a first predetermined voltage is applied to a first electrode pair of the first electrode and the second electrode, and the third electrode being configured to decompose oxygen and nitrogen oxide contained in the test gas when a voltage equal to or higher than a second predetermined voltage is applied to a second electrode pair of the third electrode and the fourth electrode;

a first current detector configured to output a first detected value correlated with a current flowing through the first electrode pair;

a first electric power supply configured to apply a voltage to the first electrode pair;

a second electric power supply configured to apply a voltage to the second electrode pair; and an electronic control unit programmed to:

(i) control the second electric power supply such that a first removing voltage is applied to the second electrode pair, the first removing voltage being a voltage equal to or higher than the second predetermined voltage, a voltage equal to or higher than a lower limit of a voltage range in which a limiting current characteristics of nitrogen oxide are expressed in the third electrode, and a voltage lower than a voltage at which a decomposition of sulfur oxide is initiated;

(ii) control the first electric power supply such that a measuring voltage is applied to the first electrode pair, the measuring voltage being a voltage equal to or higher than the first predetermined voltage and a voltage equal to or higher than a voltage at which a decomposition of water is initiated in the first electrode;

(iii) acquire the first detected value from the first current detector when the first removing voltage is applied to the second electrode pair and the measuring voltage is applied to the first electrode pair; and (iv) detect the concentration of the sulfur oxide contained in the test gas based on the first detected value.

2. The gas concentration detecting device according to claim 1, wherein the electronic control unit is configured to acquire a magnitude of the current flowing through the first electrode pair as the first detected value.

3. The gas concentration detecting device according to claim 2, wherein the electronic control unit is configured to detect a higher value of the concentration of the sulfur oxide contained in the test gas as the first detected value decreases.

4. The gas concentration detecting device according to claim 3, further comprising:

a second current detector configured to output a second detected value correlated with a current flowing through the second electrode pair, wherein the electronic control unit is configured to acquire the second detected value from the second current detector when the first removing voltage is applied to the second electrode pair, and wherein the electronic control unit is configured to detect the concentration of the oxygen contained in the test gas based on the second detected value.

5. The gas concentration detecting device according to claim 2, further comprising:

a second current detector configured to output a second detected value correlated with a current flowing through the second electrode pair, wherein the electronic control unit is configured to acquire the second detected value from the second current detector when the first removing voltage is applied to the second electrode pair, and wherein the electronic control unit is configured to detect the concentration of the oxygen contained in the test gas based on the second detected value.

6. The gas concentration detecting device according to claim 2, further comprising:

a second current detector configured to output a second detected value correlated with a current flowing through the second electrode pair, wherein the electronic control unit is configured to acquire the second detected value from the second current detector when the first removing voltage is applied to the second electrode pair, and wherein the electronic control unit is configured to detect the concentration of the oxygen contained in the test gas based on the second detected value.

7. The gas concentration detecting device according to claim 1, further comprising:

a second current detector configured to output a second detected value correlated with a current flowing through the second electrode pair, wherein the electronic control unit is configured to acquire the second detected value from the second current detector when the first removing voltage is applied to the second electrode pair, and wherein the electronic control unit is configured to detect the concentration of the oxygen contained in the test gas based on the second detected value.

8. The gas concentration detecting device according to claim 1, further comprising:

a third electric power supply, wherein the gas concentration detecting element includes a third electrochemical cell, the third electrochemical cell including a third solid electrolyte body, a fifth electrode and a sixth electrode, the third solid electrolyte body having oxide ion conductivity, the fifth electrode and the sixth electrode being arranged on respective surfaces of the third solid electrolyte body, the fifth electrode being exposed to the internal space, the fifth electrode being arranged at a position in the internal space closer to the diffusion resistance unit than the third electrode is, the sixth electrode being exposed to the second atmospheric air introduction path, and the fifth electrode being configured to decompose oxygen without decomposing the nitrogen oxide contained in the test gas when a voltage equal to or higher than a third predetermined voltage is applied to a third electrode pair of the fifth electrode and the sixth electrode, wherein the third electric power supply is configured to apply a voltage to the third electrode pair, wherein the electronic control unit is configured to control the third electric power supply such that a second removing voltage is applied to the third electrode pair, the second removing voltage being a voltage equal to or higher than the third predetermined voltage, a voltage equal to or higher than the lower limit of a voltage range in which the limiting current characteristics of oxygen are expressed in the fifth electrode, and a voltage lower than a voltage at which the decomposition of sulfur oxide is initiated, wherein the electronic control unit is configured to acquire the first detected value from the first current detector when the second removing voltage is applied to the third electrode pair, the first removing voltage is applied to the second electrode pair, and the measuring voltage is applied to the first electrode pair, and wherein the electronic control unit is configured to detect the concentration of the sulfur oxide contained in the test gas based on the first detected value.

9. The gas concentration detecting device according to claim 8, further comprising:

a second current detector configured to output a second detected value correlated with a current flowing through the second electrode pair; and a third current detector configured to output a third detected value correlated with a current flowing through the third electrode pair, wherein the electronic control unit is configured to acquire the second detected value from the second current detector when the first removing voltage is applied to the second electrode pair, the electronic control unit being configured to detect the concentration of the nitrogen oxide contained in the test gas based on the second detected value, and wherein the electronic control unit is configured to acquire the third detected value from the third current detector when the second removing voltage is applied to the third electrode pair, the electronic control unit being configured to detect the concentration of the oxygen contained in the test gas based on the third detected value.

10. The gas concentration detecting device according to claim 8, wherein the fifth electrode contains at least one selected from the group consisting of platinum, gold, lead, and silver.

11. The gas concentration detecting device according to claim 1, further comprising:

a third electric power supply, wherein the gas concentration detecting element includes a third electrochemical cell, the third electrochemical cell including a third solid electrolyte body, a fifth electrode and a sixth electrode, the third solid electrolyte body having oxide ion conductivity, the fifth electrode and the sixth electrode being arranged on respective surfaces of the third solid electrolyte body, the fifth electrode being exposed to the internal space, the fifth electrode being arranged in a region reached by test gas containing oxygen with the concentration equal to the concentration of the oxygen contained in the test gas reaching the third electrode in the internal space, the sixth electrode being exposed to the second atmospheric air introduction path, and the fifth electrode being configured to decompose oxygen without decomposing the nitrogen oxide contained in the test gas when a voltage equal to or higher than a third predetermined voltage is applied to a third electrode pair of the fifth electrode and the sixth electrode, wherein the third electric power supply is configured to apply a voltage to the third electrode pair, wherein the electronic control unit is configured to control the third electric power supply such that a second removing voltage is applied to the third electrode pair, the second removing voltage being a voltage equal to or higher than the third predetermined voltage, a voltage equal to or higher than the lower limit of a voltage range in which the limiting current characteristics of oxygen are expressed in the fifth electrode, and a voltage lower than a voltage at which the decomposition of sulfur oxide is initiated, wherein the electronic control unit is configured to acquire the first detected value from the first current detector when the second removing voltage is applied to the third electrode pair, the first removing voltage is applied to the second electrode pair, and the measuring voltage is applied to the first electrode pair, and wherein the electronic control unit is configured to detect the concentration of the sulfur oxide contained in the test gas based on the first detected value.

12. The gas concentration detecting device according to claim 11, further comprising:

a second current detector configured to output a second detected value correlated with a current flowing through the second electrode pair; and a third current detector configured to output a third detected value correlated with a current flowing through the third electrode pair, wherein the electronic control unit is configured to acquire the third detected value from the third current detector when the second removing voltage is applied to the third electrode pair, the electronic control unit being configured to detect the concentration of the oxygen contained in the test gas based on the third detected value, and wherein the electronic control unit is configured to acquire the second detected value from the second current detector when the first removing voltage is applied to the second electrode pair, the electronic control unit being configured to detect the concentration of the nitrogen oxide contained in the test gas based on a difference between the third detected value and the second detected value.

13. The gas concentration detecting device according to claim 12, wherein the electronic control unit is configured to detect a higher value of the concentration of the oxygen contained in the test gas as the third detected value increases, and wherein the electronic control unit is configured to detect a higher value of the concentration of the nitrogen oxide contained in the test gas as a difference between the second detected value and the third detected value increases.

14. The gas concentration detecting device according to claim 1, wherein the third electrode contains at least one selected from the group consisting of platinum, rhodium, and palladium.

* * * * *